United States Patent [19]

Marson et al.

[11] Patent Number: 5,077,486
[45] Date of Patent: Dec. 31, 1991

[54] POWER SUPPLY FOR CATHODIC PROTECTION SYSTEM

[76] Inventors: Gary Marson, 15 Howard Drive, Willowdale, Ontario, Canada, M2K 1K4; Art W. Gaber, 10334-172 Street, Edmonton, Alberta, Canada, T5S 1G9

[21] Appl. No.: 170,741

[22] Filed: Mar. 21, 1988

[51] Int. Cl.$^5$ .................................... C23F 13/00
[52] U.S. Cl. .................................. 307/95; 204/196; 204/147
[58] Field of Search .................. 367/95; 204/147, 196, 204/99, 197, 148; 324/65 CR, 425, 436, 442; 363/16, 18

[56] References Cited

U.S. PATENT DOCUMENTS

| | | | |
|---|---|---|---|
| 3,622,489 | 11/1971 | Dumitrescu et al. | 204/196 |
| 4,035,268 | 7/1977 | Hote | 204/99 |
| 4,080,272 | 3/1978 | Ferry et al. | 204/147 |
| 4,383,900 | 5/1983 | Garrett | 307/95 X |
| 4,437,065 | 3/1984 | Woudstra | 324/65 CR X |
| 4,587,479 | 5/1986 | Rhoades et al. | 324/65 CR |
| 4,592,818 | 6/1986 | Cavil et al. | 204/196 |
| 4,664,764 | 5/1987 | Zofan | 307/95 X |
| 4,780,189 | 10/1988 | Ridgley | 204/196 |

Primary Examiner—A. D. Pellinen
Assistant Examiner—Sharon D. Logan
Attorney, Agent, or Firm—Fay, Sharpe, Beall, Fagan, Minnich & McKee

[57] ABSTRACT

A power module for a cathodic protection system is provided having a switch-mode power circuit and a synchronous switch assembly. The method of the invention comprises rectifying an alternating utility power signal with a power transformer and switch assembly. The switch assembly is controlled by a phase control circuit to provide a selective controlled phase delay to provide a 0-100% range power signal to the load selectively operable in a constant current, constant voltage or off-potential manner.

14 Claims, 17 Drawing Sheets

22.5° PHASE DELAY

90° PHASE DELAY

135° PHASE DELAY

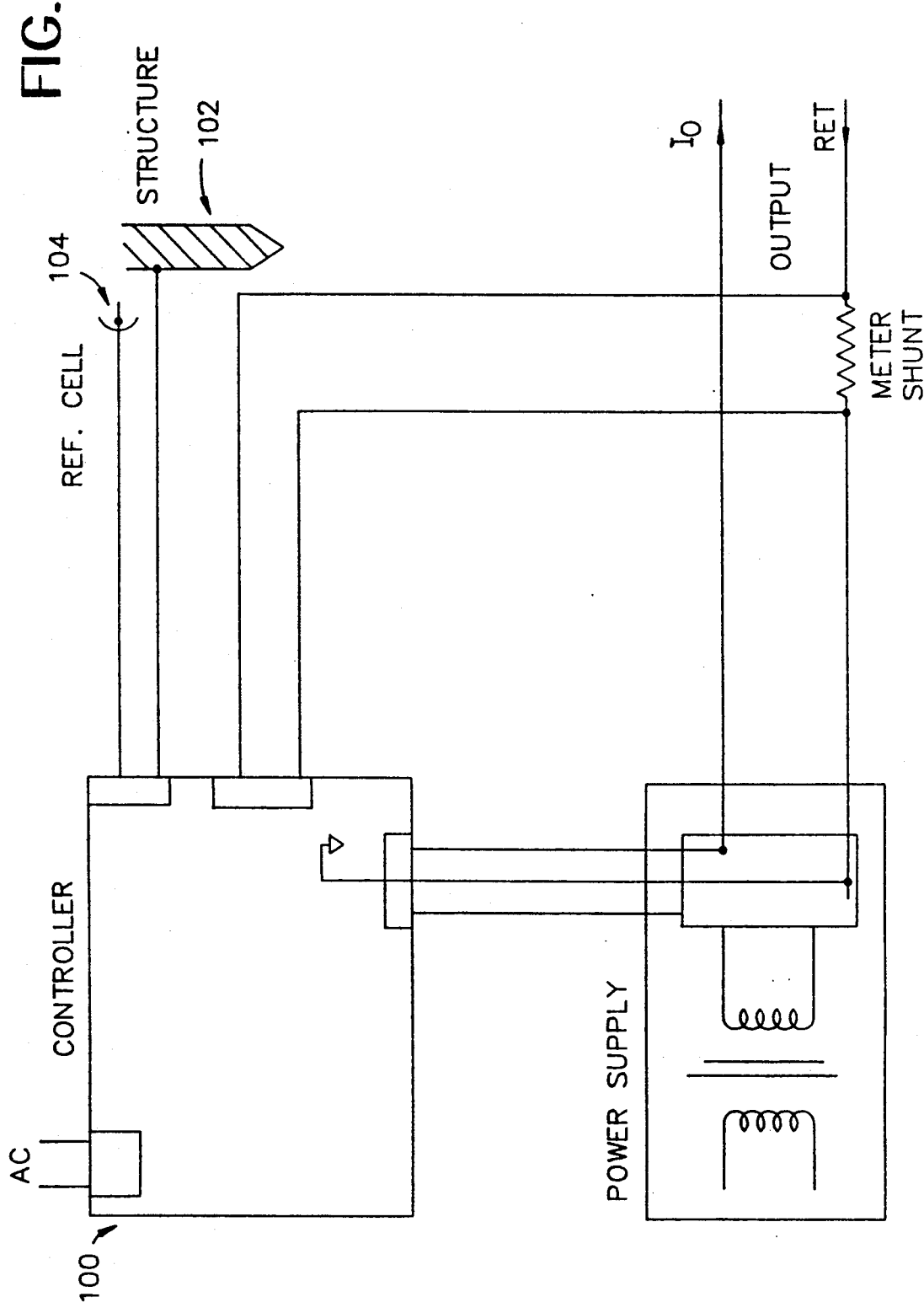

POWER SUPPLY FOR CATHODIC PROTECTION SYSTEM

BACKGROUND OF THE INVENTION

This application pertains to the art of cathodic protection and more particularly, to the regulation of current and voltage impressed upon a structure in order to protect the structure from corrosive effects of the environment.

The invention is particularly applicable to the protection of metal and concrete structures such as road overpasses, storage tanks, pipelines, bridges and parking garages.

Cathodic protection techniques have traditionally used a direct current impressed across the surface of a structure that is to be protected from the usual corrosion processes occurring in soil or concrete. Ideally, the current level is maintained at a value just sufficient to halt the electrochemical corrosive reactions occurring at the surface of the structure. The criterion for determining the degree of protection from corrosion is the value of the voltage of an electrochemical half-cell "barrier" existing at the structure/soil interface. This barrier is built up and maintained by passing a D.C. current through the structure/soil interface.

Cathodic protection systems have been comprised of a large 60 Hz power transformer with selectable winding taps followed by a diode rectifier bridge and a filter arrangement to produce a D.C. voltage. The selectable tap adjust system permits varying the applied D.C. voltage. This voltage is applied to an electrode arrangement buried in the ground near the structure being protected. The technique is simple and has been widely used within the industry. In these systems, the lack of electronic feedback control necessary to compensate for varying soil conditions may render the tap adjust system ineffective since the taps, if changed at all, are changed by field service personnel at infrequent intervals. Also, since such manual systems are typically inefficient and not automatically adaptable to a widely varying load, they have to be specially designed for each application, and even then, oftentimes cause unnecessary anode consumption because of their inability to assess and adapt the proper energy requirements for the system.

Another consequence of the tap adjust or phase controlled technique is the mandatory use of large 60 Hz power transformers. The transformers are used to step down the utility voltage to the comparatively low voltages used in cathodic protection. The transformer also provides safety isolation between the utility line and power supply output. These transformers are typically quite heavy and bulky. Additionally, in order to control efficiency, a different transformer must be designed and built for each different set of customer requirements. The transformer must be designed to match the utility power to the particular worst case voltage and current ranges in the customer specification. It is, therefore, difficult to use two or three standard transformer designs to meet all production demands.

Another system used in the industry comprises phase controlled rectifiers between the power transformer and the filter. Phase controlled rectifiers allow the use of electronic feedback control to regulate the current and voltage passing into the protection electrode system. At present, phase controlled rectifier circuits are the industry standard for applications requiring unattended regulation of current flow in cathodic protection systems.

Another consequence of using 60 Hz power transformers is in order to obtain reasonably low ripple (i.e. steady D.C. current) of the power supply output, some filtering must be included between the phase controlled rectifiers or diode bridge and the output to the electrodes. Since the controlled rectifiers are pulsed at line frequency (60 Hz), the filter capacitor (and possibly inductor) must be fairly large.

A third method of assessing the cathodic protection is to measure the barrier potential at the structure/soil interface. Since the barrier is really a chemical half-cell, a voltage measurement must be made using a second standard "reference" half-cell. The actual measurement of the barrier potential is made with respect to the standard reference cell.

The barrier half-cell is connected to the reference half-cell electrically by the conductivity of the soil or concrete between the surface of the steel and the active surface of the reference half-cell.

The reference half-cell is small and is usually located at a convenient location nearby the surface that is to be protected. Using a high input impedance voltmeter connected between the structure interior and the terminal of the reference cell which is not contacting the soil, the barrier potential of the structure can be measured with respect to the half-cell used. The variation in a well-built reference is very low with time and temperature.

Often, large uncontrollable errors are introduced into the measurement of the true barrier potential. The chief source of error is a voltage drop existing in the volume of the soil between the steel structure and the location of the reference half-cell. The voltage drop results from the product of electrical soil currents flowing in the vicinity of the structure - reference cell volume and the electrical resistance of the soil. This is called "IR Drop".

This IR drop represents a voltage generator separating the reference half-cell from the steel. The result is a measurement error in the voltage between the reference half-cell and the structure interior. The amount of the error is exactly equal to the IR drop in the soil between the structure and reference cell. The IR drop may be positive or negative, depending on the direction of the currents flowing in the soil.

One prime source of IR drop error is the flow of the actual cathodic protection current itself. Thus the protecting current masks the measurement of its own effectiveness. The IR drop varies with the level of the cathodic protection current and with the soil resistance. Soil resistance may change with time due to moisture variations.

One strategy for minimizing the IR drop is the placement of the reference half-cell physically close to the steel structure to be protected. This is usually inconvenient and costly especially in structures that are deep underground or have a large physical extent. The advantage is that the soil volume, and hence the soil resistance, is decreased. The voltage error would be decreased for IR drop due to cathodic protection current.

Recent research in cathodic protection chemistry indicates that a more representative measure of the "health" of the structure may be obtained by decreasing the cathodic current to zero very quickly (less than a millisecond) and taking a reading of the barrier potential of the structure within a very short interval (10's of milliseconds) after the current has been brought to zero. Due to the size of the filter components used in the phase controlled and diode bridge rectifier systems this "instant off" capability cannot be achieved, since the time required to discharge the energy contained in the filter can amount to 10's of milliseconds. In such circuits, the filter will discharge into the electrode system which thereby precludes a practical "instant off" feature. Instant off can only be achieved with rectifiers pulsing essentially directly into the electrode system with no D.C. filtering.

As noted above, an attractive alternative is the method of measuring the "true" barrier potential while the cathodic protection current is zero. Thus the protection current must be interrupted periodically and a voltage measurement taken between the reference half-cell and the structure barrier half-cell.

The resulting voltage is called the "Off Potential". The Off Potential (O.P.) is a much more representative measurement of the protection barrier voltage and an accurate representation of the health or effectiveness of the barrier. On the basis of the O.P., an electronic control system may be used to control the cathodic protection current supplied to the barrier to maintain a desired barrier potential. The desired value of the barrier potential is determined by chemical considerations and is assessed by a Chemical Engineer.

The general method of adjusting the protection current level by comparing the measured voltage of the structure-to-reference to a manually commanded or set voltage is called "auto-potential" control in the industry. As explained above, IR drops are due to the cathodic protection current itself (plus any unrelated interference currents) and may corrupt the measurement of the barrier potential.

A strong interest has developed for improved corrosion protection in concrete structures such as road overpasses, bridges and parking garages. These structures require generally more precise control of cathodic protection current and different parts of the structure must be protected by independently regulated channels.

Presently, if it is desired to protect separate zones, a structure of conventional technology requires the use of a separate rectifier for each zone of the structure. Or, dissipative rheostats must be used from a single rectifier to divide and distribute the single rectifier output to various zones of the structure. Both techniques are costly and overall inefficient. Also the rheostat approach requires periodic adjustment by service personnel.

Although switch-mode power circuit technology is conventionally known for applications such as computer-related circuit powering or other high speed electronics, it has not been employed in the cathodic protection industry. One reason for avoiding its application is that it is not expected to be useful in a broad situation that is widely variable from 0 to 100% power capacity. Also since cathodic protection is usually current intensive, those skilled in the art were normally suspect that switchmode power circuit technology which primarily useful in low current applications could be adapted for cathodic protection systems.

A conventional forward convertor switchmode power supply uses a power transformer with a power switching transistor connected to the primary and a diode rectifier connected to the secondary or output winding. The output rectifier is followed by an L-C filter to produce a smooth D.C. output during the time that the power switching transistor is ON, an input supply is connected across the primary and power is transferred to the output through the rectifier diode. When the power transistor is turned OFF, the flow of power through transformer is stopped. The output inductor current continues to flow through a catch diode. When the power transistor is turned on again, the inductor current will flow through the rectifier D1 and the secondary winding of the transformer. If we assume that the inductor current is fairly constant and greater than zero at all times, the D.C. output voltage will be equal to the (input line voltage) × (transformer turns ratio) × (duty ratio).

The duty ratio is the fraction of the time that the power transistor is on. The D.C. output voltage may be controlled by varying the duty ratio.

The forward converter is an example of a buck regulator. Other types of buck regulators include push-pull converters, half-bridge, or full-bridge pulse-width modulated circuits or even current-fed push-pull converters. The common factor in buck regulators is that the input line is chopped by a power transistor (with or without a power transformer) and the resulting chopped voltage waveform is fed to an L-C output filter. The L-C filter basically filters out the A-C part of the chopped waveforms and allows only the D.C. content of the waveform to be presented to the output. By using the power transistor duty ratio to vary the D.C. content of the chopped waveform, we can vary the D.C. output.

The above-approach works well in most power supply applications. However, at very low output load currents, the unavoidable current ripple in the output filter inductor causes the inductor current to hit zero during part of each switching cycle. This condition causes the relationship between D.C. output voltage and duty ratio to change, the net result being that the control of the output voltage becomes difficult at low output currents. In most applications a minimum load is specified to avoid this effect. Cathodic protection applications see instances where load current drawn can be significantly less than 10% of maximum output. Otherwise, unnecessary anode consumption and shorter system life is the result.

Another problem with conventional systems occurs at low load resistances approaching short circuit. If the pulse width is being controlled to produce constant output current, then as the load resistance decreases, the output voltage must decrease. To decrease the output voltage, the pulse width must be lowered. There is a limit to which the pulse width can be lowered in constant frequency pulsewidth modulated switching power supplies. It is difficult to control the output voltage below approximately 5% of maximum output voltage depending on input line and frequency of operation.

The present invention contemplates a new and improved cathodic protection system and method which overcomes all of the above referred to problems and others to provide a new protection system which improves the quality of the cathodic protection for a structure while being readily adaptable to a plurality of uses with systems for a wide variety of structural items.

BRIEF SUMMARY OF THE INVENTION

A synchronous detector method of rectification has been developed to avoid the problems of present diode bridge, phase controlled and auto-potential systems at extremes of load resistance. Three modes of operation are obtainable with the present invention, namely, constant current, constant voltage and auto-potential.

A suitable switch-mode power circuit is used to produce a square wave on the secondary of the power transformer. The frequency of the square wave is fixed and is usually between 40 Khz and 100 Khz. A center-tap secondary winding is used to create two square waves 180° apart when measured with respect to the center tap.

Instead of the usual diode rectifiers between the secondary winding and the output L-C filter, two ideal switches are inserted. The switches are two poles of a double pole-double throw type switch. They are ideal in the sense that they may be switched from one state to the other instantaneously, and when closed, they have zero resistance allowing current to flow both ways.

The switch is controlled by an electronic signal from phase controlling circuitry. The control signal is arranged to be a 50% duty ratio so that the switch spends equal time in each position. The frequency of the control signal is also the same as the square wave on the secondary of the power transformer. The only free parameter that is allowed is the phase shift between the transformer voltage and the control signal to the ideal switch.

Since negative voltage is available to the inductor input during part of the switching cycle and current can flow both ways through the switches, the current in the output inductor need never go discontinuous, even at zero output load current. This allows full control of output voltage even at open circuit conditions.

In fact, output voltage can be negative with the proper amount of phase shift. With 90° of phase shift, the average of the output voltage may be zero. So zero output voltage is a normal output value between maximum negative and maximum positive output.

The average of output voltage can be adjusted to zero when the output is shorted. This will allow control even when the inductor current is at any steady value; positive, negative or zero. Normally, an external feedback control loop will automatically adjust the phase shift continuously to maintain a commanded output voltage or current.

The design intent was to allow paralleling of similar power modules to boost output current capability. A current control feedback scheme was used to vary the phase shift. The output filter inductor current is measured by some suitable means and compared to a current demand input signal. The phase shift is varied in the proper direction to vary the output voltage of the module to achieve the commanded level of output current.

Since only positive output current is required for cathodic protection, an alternative switching arrangement may be implemented whereby the negative output current capability of the general scheme is eliminated. The synchronous MOSFET switches are now only unilateral. This simplification cuts the parts count. The tradeoff for this lower complexity approach is that the output current cannot be reduced completely to zero.

In practice the output current can be reduced to less than 200 mA. For a full scale output current of 25A, this minimum current amounts to 0.8% of full scale, which is more than adequate for practical applications.

The present control circuit for implementing "Autopotential" control uses the "instant off" method. The control circuit turns off the cathodic protection current, and takes a measurement of the true or "Off Potential" of the protection barrier. Thus the IR drop error due to the cathodic protection current is completely eliminated.

The present invention is also designed to reject measurement errors caused by IR drops due to unrelated A.C. or rectified pulsating D.C. currents flowing in the soil volume between the reference cell and the steel structure.

The power supply for the cathodic protection current is a high speed switch-mode type power supply. The advantage of this type of supply, besides very low volume, is the fact that it may be switched on and off very quickly. The cathodic protection current may be turned off from full to zero within 2 to 5 milliseconds and turned on within 2 milliseconds.

In the auto-potential mode, the control circuit may command the "instant off" of current from the power supply, take the O.P. measurement, store the measurement, calculate the error from the setpoint, and turn the protection current back on.

The advantage of the "instant off" feature is that the barrier potential may be measured very quickly after nearly instant removal of the protection current. In smaller structures, the barrier potential may change very quickly and it is an advantage to be able to shut off the current instantly and take a voltage reading within milliseconds.

Conventional rectifiers used to supply the protection current are usually filtered at the output to provide a relatively smooth D.C. output. Using 60 Hz phase control techniques, these units cannot be turned off from full to zero output for several 10's of milliseconds. The same is true for turn on.

The present control circuit is designed to turn off the protection current for a total of 20 milliseconds during which time O.P. measurements are taken and stored. The process is repeated every second.

Thus, the barrier is sampled frequently enough to follow changes, the barrier potential is sampled very quickly to eliminate "potential sag" errors, and the total current "off time" is very short to minimize the duty ratio (20 milliseconds out of 1 second).

The present control circuit is also designed to discriminate against powerline frequency related noise currents. During the time that the cathodic protection current is turned off, two voltage measurements of the O.P are taken. The measurements are taken at the next two zero-crossing points of the local A.C utility line. The two measurements are stored and then averaged before being compared to the setpoint value.

The rational for this technique is as follows: any A.C. or pulsating D.C. currents flowing in the soil are likely related to the instantaneous A.C. waveforms of the local power utility. These currents will reach zero during the zero crossing of the voltage on the utility line. To cater for the possibility that the currents are phase shifted from the utility voltage waveform, two samples are taken on alternate zero crossings (8.333 milliseconds apart) and averaged. Thus line related noise will be cancelled out. This holds true even if three phase currents are present. Thus line-related currents flowing in the soil will be rejected in the determination of O.P.

One type of interference current that the present control system will not reject is a steady unrelated and non line-related D.C. in the vicinity of reference half-cell. This type of current, it is unknown, cannot be compensated for. The only solution is a more advantageous placement of the reference cell, or diversion of the interfering current.

In general, this control circuit, or probably any other control circuit, will not be able to detect IR drop voltage error in the O.P. due to unknown interference currents that are unrelated to the local utility power line.

One benefit obtained by use of the present invention is a cathodic protection systems which can provide a wide range of selected output energies to a wide range of loads extending from a short circuit at the output to a fully open circuit.

Another benefit of the present invention is a protection system which has a particularly fast response time. Because of the high frequency techniques used, the filter element in the power supply have relatively low values. This enables the control system response time to be under one or two milliseconds for effective implementation of "instant off" techniques. In addition, fast control loops are implemented for compensating fast transient stray currents.

Yet another benefit of the subject invention is a high efficiency system. At full output voltage and current, the switch assemblies of the subject invention offer efficiencies approaching 90%.

Yet another benefit of the subject invention is that by having a full range capability, the subject inventive system allows for modular design and parallel operation to build up a cathodic protection system capability to satisfy a wide variety of customer requirements without special design adaptation.

Other benefits and advantages for the subject new cathodic protection system and method will become apparent to those skilled in the art upon a reading and understanding of this specification.

BRIEF DESCRIPTION OF THE DRAWINGS

The invention may take physical form in certain parts and arrangements of parts, the preferred and alternative embodiments of which will be described in detail in this specification and illustrated in the accompanying drawings which form a part hereof and wherein:

FIG. 2 is a set of timing diagrams illustrating the synchronous detection in combination with a controlled phase delay operational features of the circuit of FIG. 1.

FIGS. 4A-4C comprise a schematic of the power module on the primary side of the power transformer and essentially is a switchmode power circuit, FIG. 5A-5C comprise the secondary side of the power transformer and further illustrates the synchronous detector switch assembly of the present invention;

FIG. 9 comprises a simplified schematic of a system having the analog control feature for off-potential adjustment of the system.

DETAILED DESCRIPTION OF THE INVENTION

Figure 1:
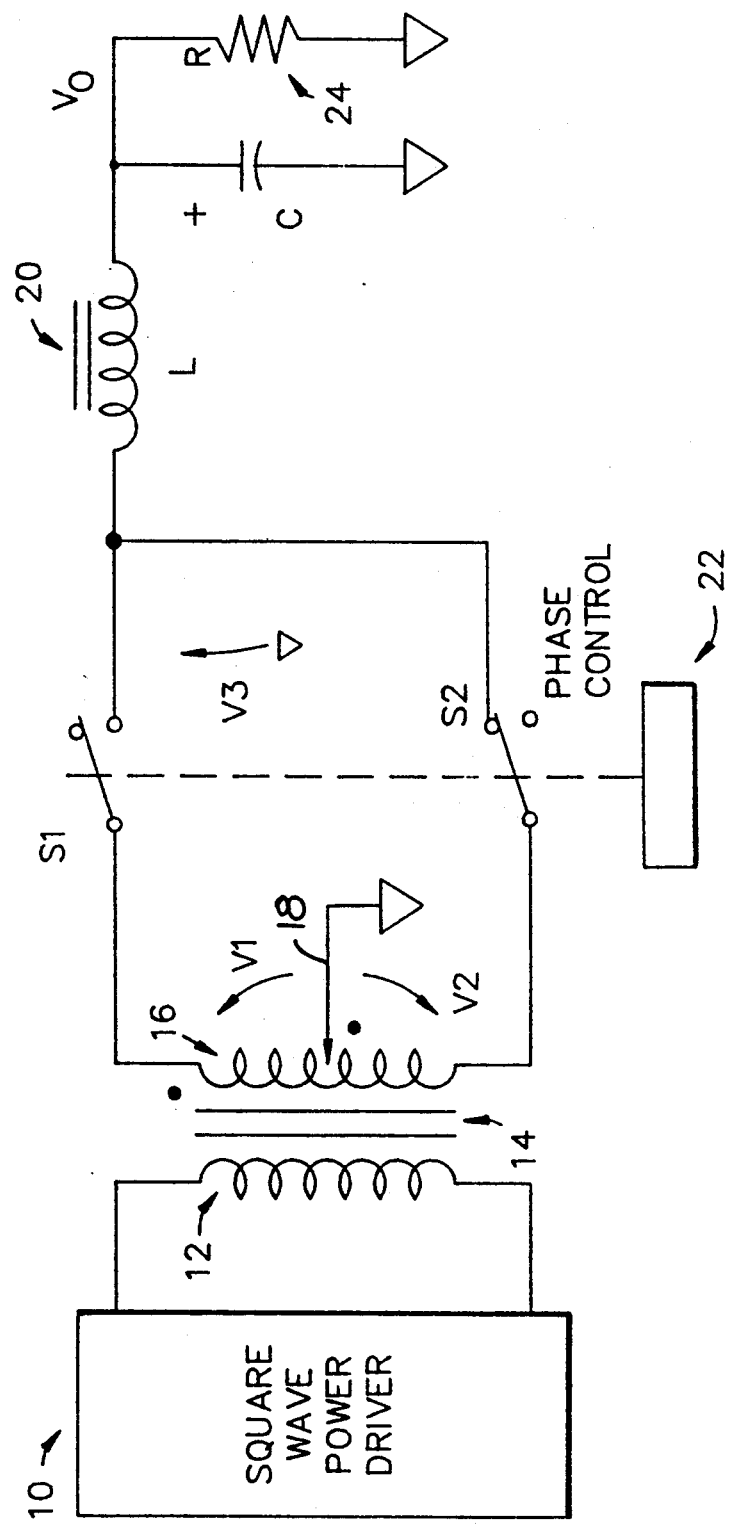
FIG. 1 is a simplified schematic of a control system for cathodically protecting a load formed in accordance with the present invention.

Referring now to the drawings, wherein the showings are for purposes of illustrating the preferred and alternative embodiments only and not for purposes of limiting same, the FIGURES show an assembly for cathodically protecting a structure by impressing a selective electrical potential with high frequency switching.

More particularly, and with reference to FIG. 1, a square wave power drive circuit 10 receives a source 12 of an alternating voltage power signal such as a conventionally accessible utility line. The drive 10 converts the alternating voltage power signal into a square wave voltage signal for communication to the primary side 12 of a power transformer 14. Preferably, the square wave power driver 10 is a switch mode power circuit which will be described in detail hereafter. The frequency of the square wave is fixed and is usually between 40 KHz and 100 KHz. A tap 18 on the secondary side winding 16 divides the square wave voltage on the power transformer and produces a plurality of selectively phased differentiated square wave voltages. Preferably, a center tap secondary winding is employed to create two square wave 180° apart when measured with respect to the center tap; however, it is within the scope of the invention to employ a multiple tap when necessary or advantageous. Instead of the usual diode rectifiers between the secondary winding 16 and the output LC filter 20, two ideal switches, S1 and S2 are inserted. The switches are preferably two halves of a double poledouble throw type switch. They are ideal in the sense that they may be switched from one state to the other instantaneously, and that when closed, they have zero resistance and allow current to flow both ways. Alternatively, it is within the scope to use unidirectional switches to reduce the component parts. The switches operate to selectively rectify the phase differentiated square wave voltages. The switches are controlled with an electronic signal from a phase control circuit 22 that selectively delays the rectifying of the phase differentiated square wave voltages by delaying the operation of the switches relative to a frequency of a differentiating square voltages. The delaying comprises a controlled phase delay time. Preferably, the control signal is arranged to be a 50% duty ratio so that the switch spends equal time in each direction. The frequency of the control signal is preferably the same as the square wave on the secondary of the power transformer. The only free parameter that is allowed is the phase shift or delay between the transformer voltage and the control signal to the switches S1, S2. The structure that is being protected is represented by the resistance 24.

Figure 2A:
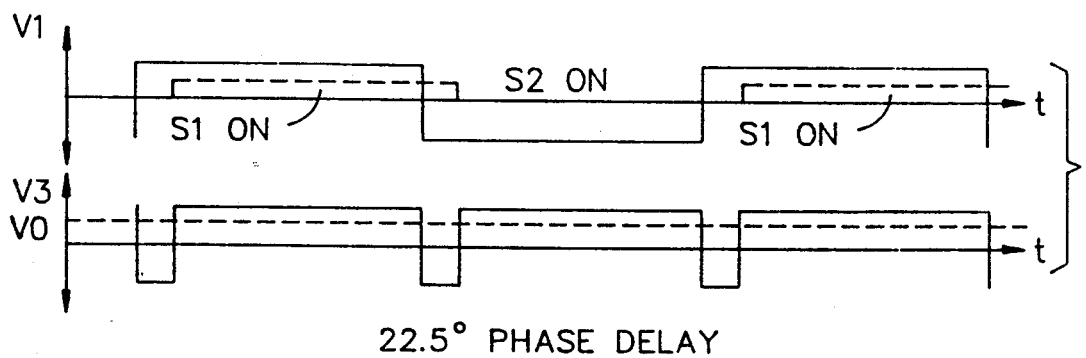
FIG. 2A illustrates a 22.5 degree phase delay.
Figure 2B:
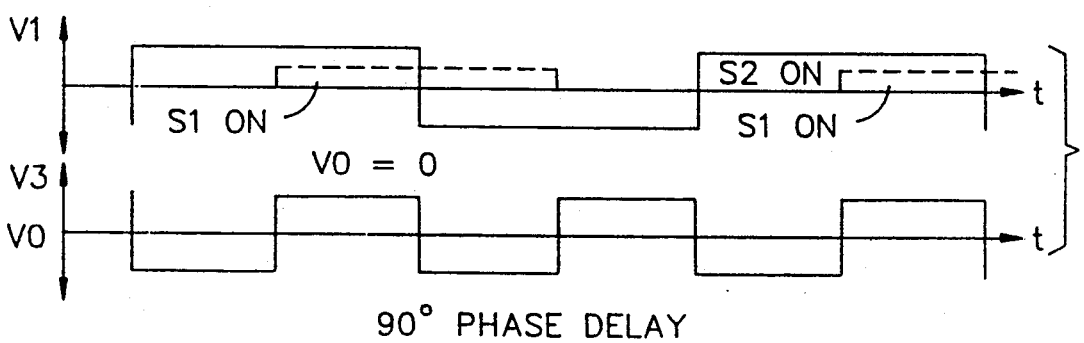
FIG. 2B illustrates a 90 degree phase delay.
Figure 2C:
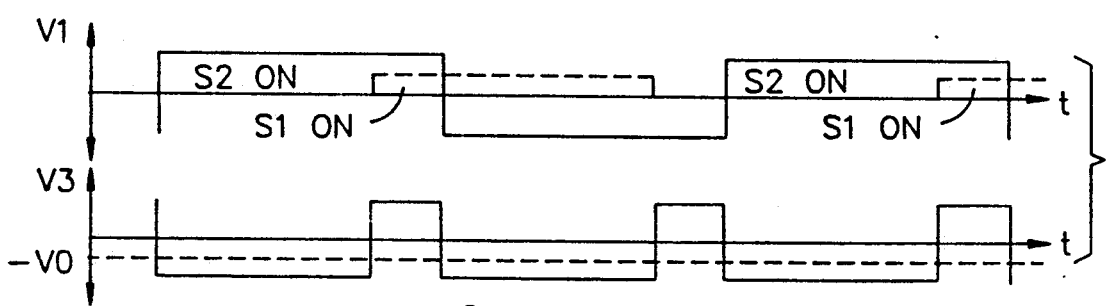
FIG. 2C illustrates a 135 degree phase delay.

FIG. 2 illustrates some of the waveforms involved for selective phase delays. While the FIGURES only illustrate V1, V3, and V0 (FIG. 1), it can be appreciated that V2 is the complement of V1. With reference to FIG. 2A, a 22.5° phase delay is imposed by the phase control 22 on the switches so that the load will see a positive D.C. voltage V0. It can be seen that the switches are delayed relative to the frequency of the square waves from the secondary side of the power transformer 14. Accordingly, it will be seen that switching is not coincident with the alternating voltage, but is delayed relative thereto so that while the switch is closed the current will alternate to the load with a preselected controlled phase delay. Where a 22.5° phase delay is involved, a small portion of the voltage signal to the load is not rectified corresponding to the phase delay, this reduces the D.C. voltage to the load, V0 from full power, V1. FIG. 2B illustrates how a 90° phase delay can be used to provide a zero D.C. voltage to the load, while FIG. 2C illustrates how a 130° phase delay can provide a negative D.C. voltage to the load. V0 is shown as a D.C. voltage due to the filtering effect of the output filter 20.

Thus, the substantial benefit of the present invention, a full range of power capacity to a load is available with the subject invention.

Figure 3:
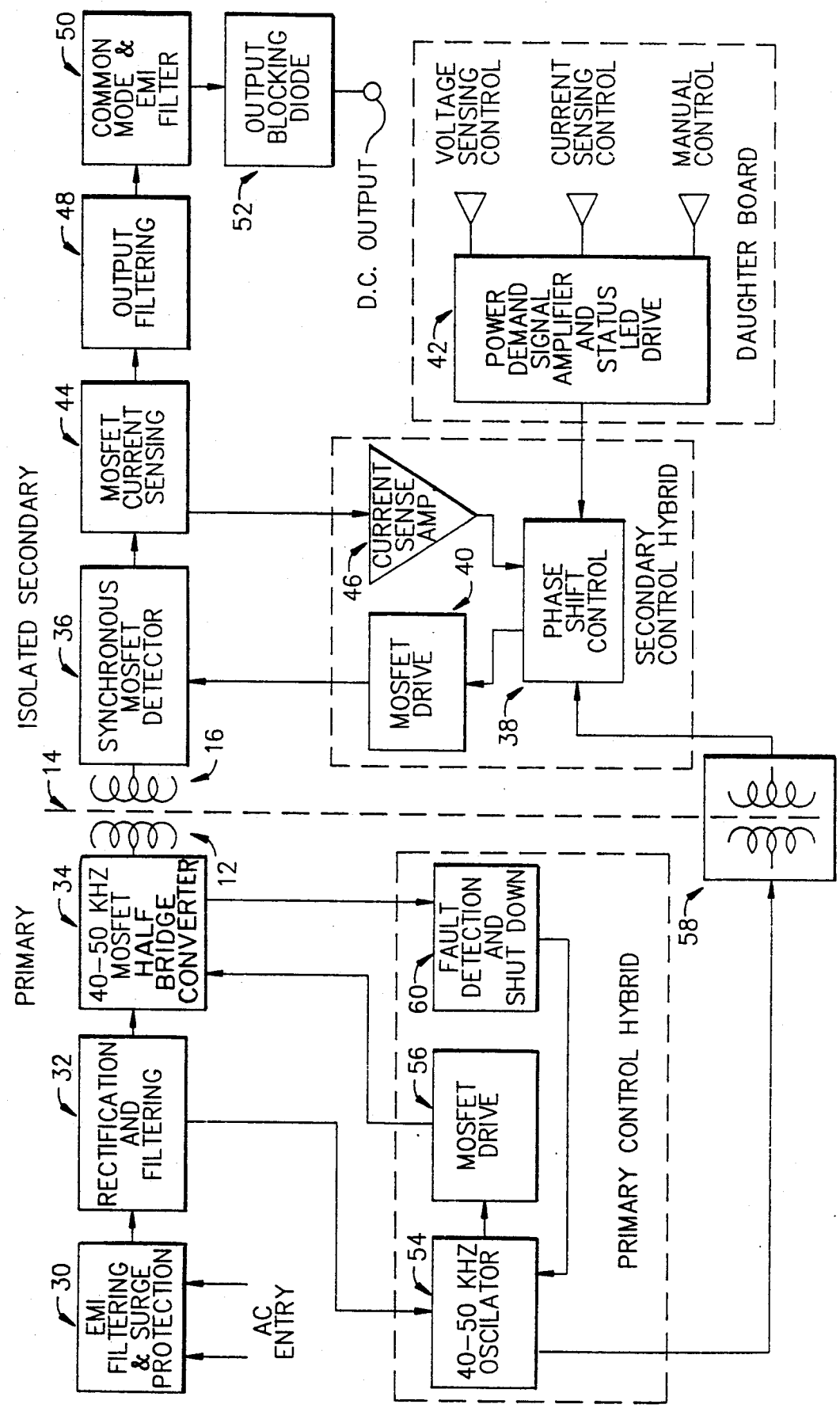
FIG. 3 is a block diagram more particularly illustrating the subject invention.
Figure 4A:
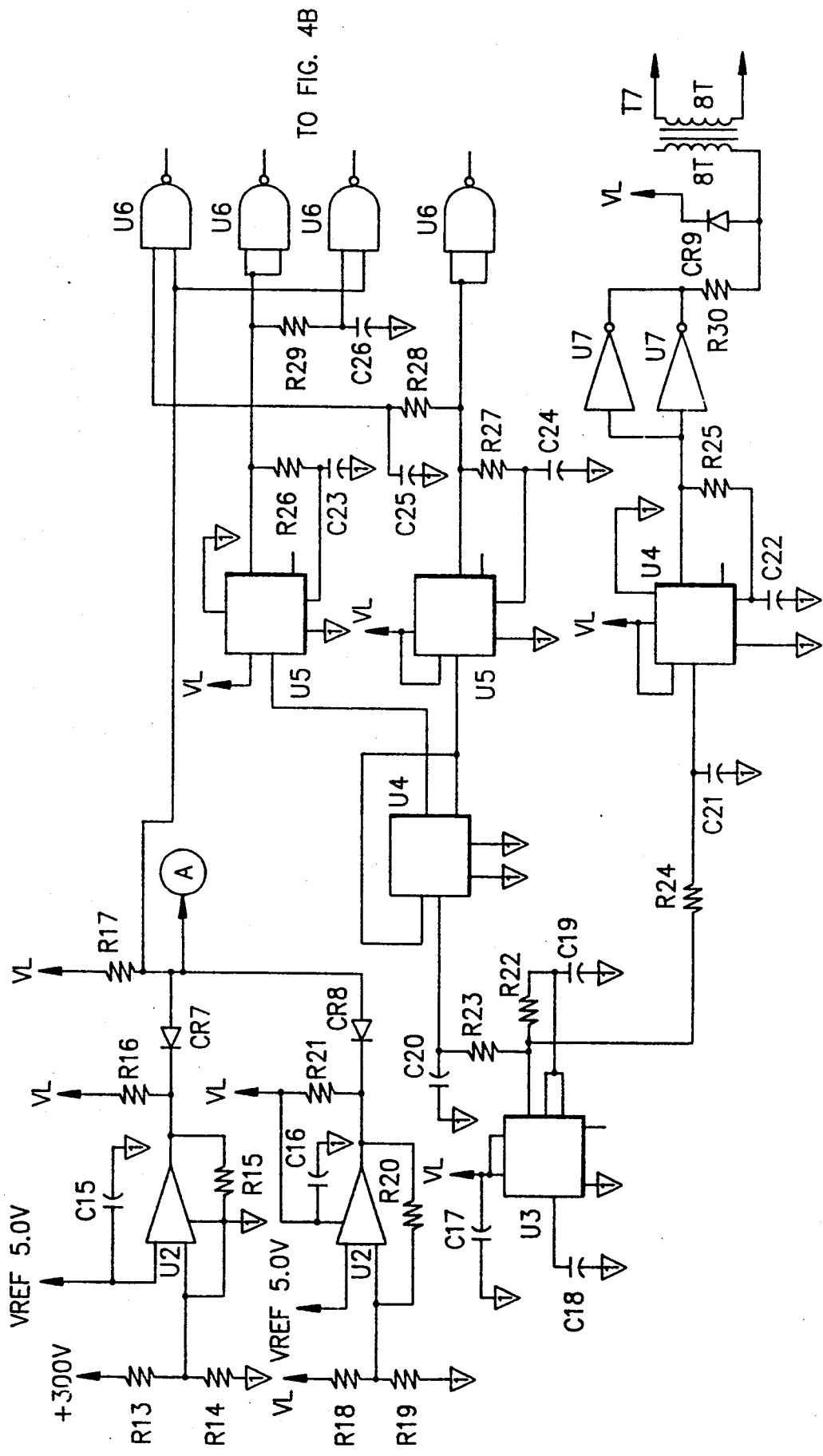
FIGS. 4A-4C and 5A-5C comprise a detailed schematic of the system illustrated in block in FIG. 3.
Figure 4B:
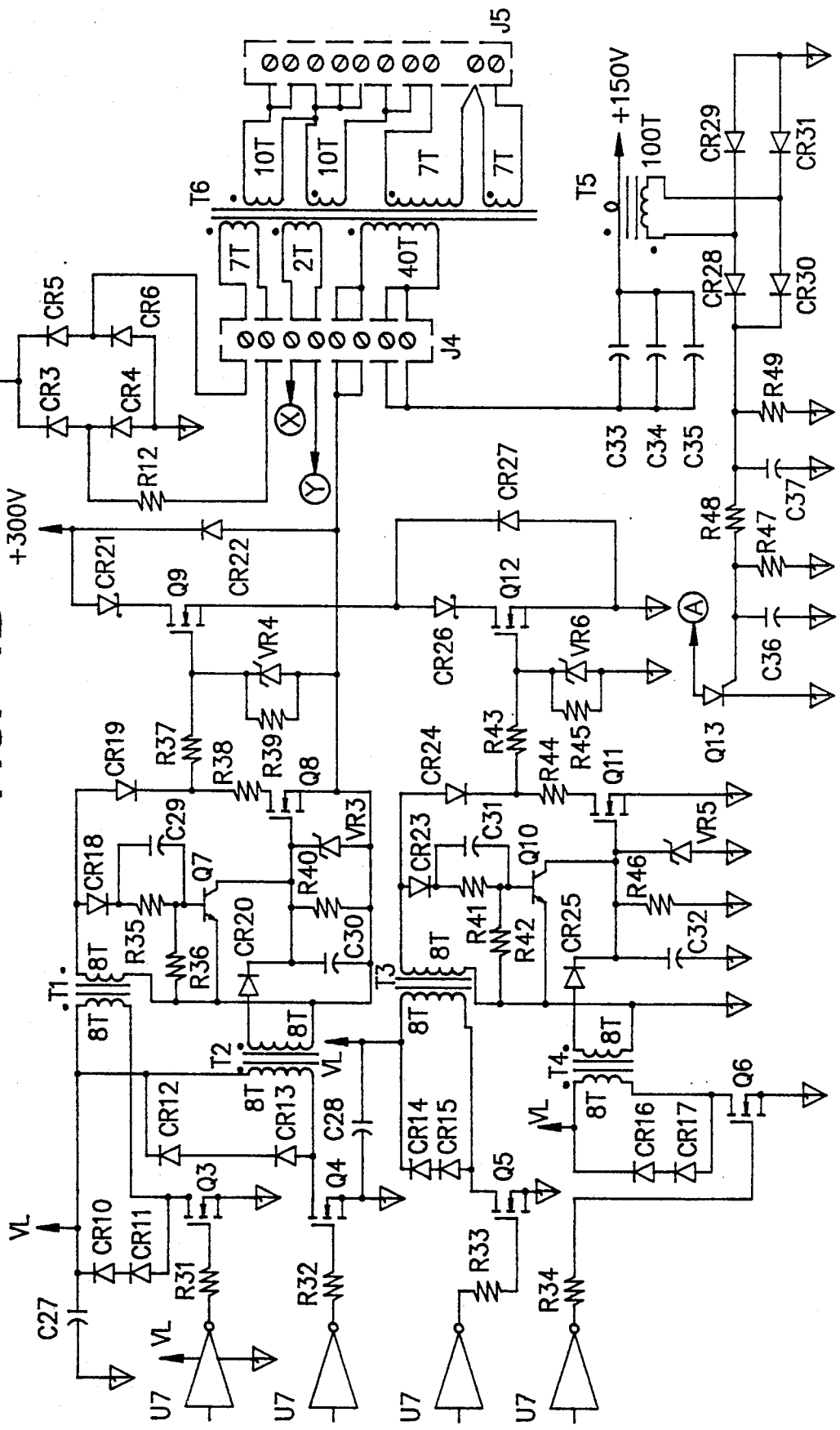
Figure 4C:
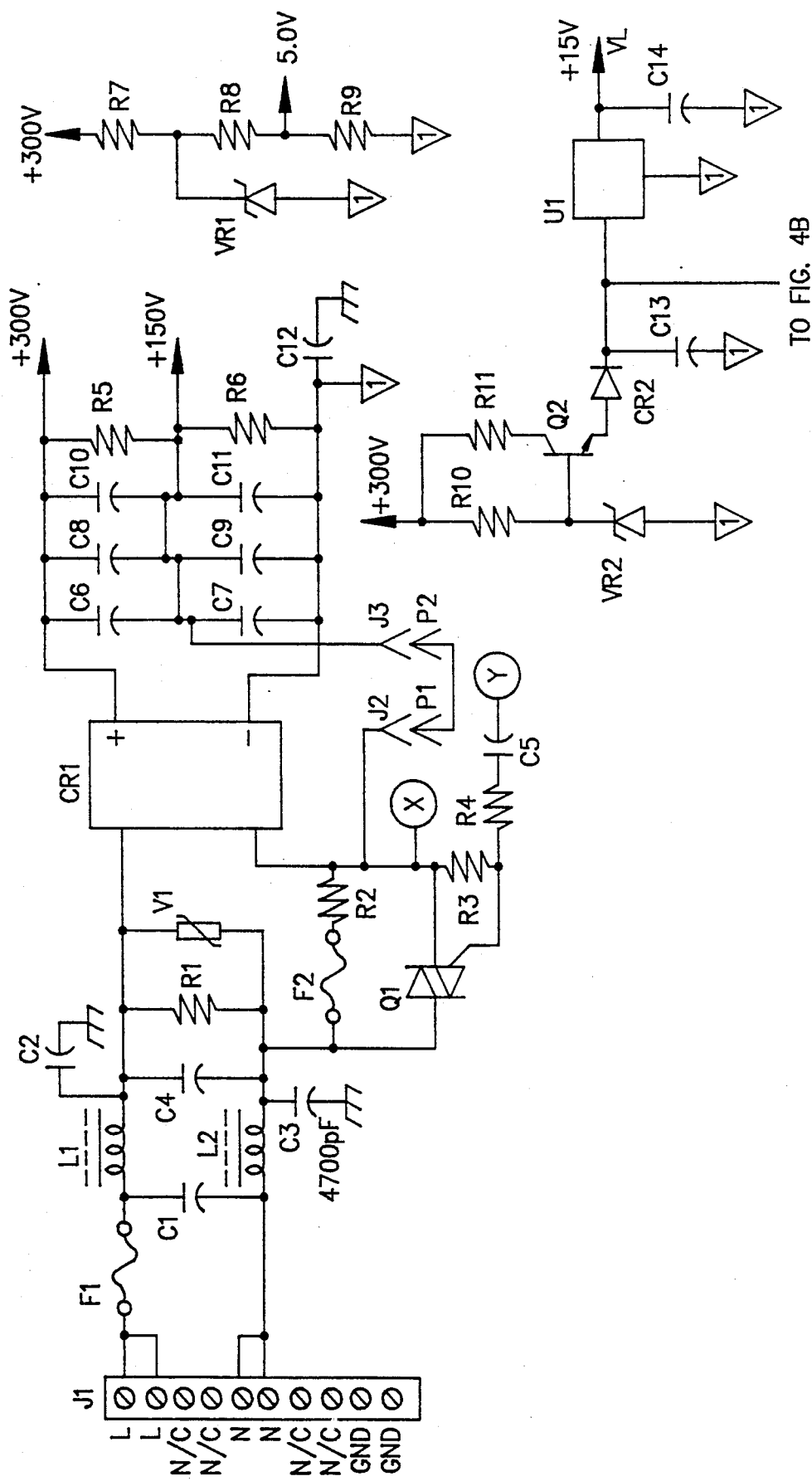

With reference to FIG. 3, a more detailed block diagram of a commercially practical circuit embodying the subject invention is shown. The source of power from a convention utility line is shown as "A.C. entry". An electromagnetic interference filtering and surge protection circuit filters the circuit for rectification and filtering 32 to produce the preferably 40 to 50 KHz square wave voltage 34 that is impressed on the primary side 12 of the power transformer 14. On the secondary side 16 of the transformer the ideal switches are included in a synchronous MOSFET detector circuit 36. The opening and closing of the switches are controlled in the secondary control hybrid by a phase shift control 38 and a drive circuit 40. It is a feature of the invention that the drive voltage and current can be adjusted to provide a constant current or a constant voltage. In particular, the daughter board shown in FIG. 3 includes devices for either voltage sensing, current sensing, or manual control of a power demand signal amplifier circuit 42 for selectively controlling the phase shift control and ultimately selectively controlling the switches in the synchronous MOSFET detector 36. The power demand signal amplifier contains a set point which is compared with the sensed impressed energy on the structure, either voltage or current, to adjust the phase shift. The current output of the synchronous MOSFET detector 36 is sensed in a MOSFET current sensing circuit 44 and amplified in an amplifier 46 for comparison with the preset desired energy control signal from the demand signal amplifier 42. A conventional output filtering circuit 48, electromagnetic interference and common node filter 50, and output blocking diode circuits 52 communicate the appropriate power signal to the D.C. output for the structure being protected.

In order to have a synchronous control of the square wave voltage signal with the phase shift control, a primary control hybrid including an oscillator circuit 54 is in communication with a synchronous control transformer 58. The MOSFET drive 56 and the fault protection and shut-down circuit 60 provide the protection circuit to prevent circuit damage in case failure of the rectification and filtering circuit 32.

With reference to FIGS. 4A-4C and 5A-5C, one detailed embodiment of a circuit including the subject invention is shown. Fuse F1 is used as the protection device on each module. The filter capacitor bank C6-C11 is charged from the A-C line through the diode bridge CR1. A 0.100 ohm series resistor, R2, is inserted in the A-C neutral. The resistor is used to limit the charging current from the A-C line to approximately 3A peak inrush when the A-C line is applied to a discharged capacitor bank. When the capacitor bank is eventually charged to a voltage sufficiently high to allow the converter to operate, the converter is turned on.

Converter turn-on results in a 50 Khz square wave existing on all windings of the main power transformer T6. One winding is brought out and used to drive the TRIAC Q1 ON. Q1 is connected in parallel with the surge limiting resistor R2. When Q1 is turned ON, there is essentially a short circuit between the A-C line and the diode bridge. Thus the low power dissipation connection to the A-C line is made after the capacitor bank is charged. The TRIAC is driven on at 100 Khz, which is essentially continuous drive. Drive circuit R4 and C5 is a high pass differentiator circuit to pass only short pulses to the TRIAC gate terminal. This is done to decrease power dissipation in the gate circuit of the TRIAC. R3 is used to bleed TRIAC leakage current to prevent inadvertent turnon.

The fuse, F2, in series with limit resistor R2 is used to protect R2 and the rest of the circuit in the event of an open circuit failure of the TRIAC Q1. The capacitor bank will charge through R2 until the converter turns on. If the converter is turned on with Q1 failed OFF, the power supply will attempt to draw all input power through R2, thus destroying the resistor and causing a flame safety hazard.

An on-board EMI filter is made up of C1 through C4 and inductors L1 and L2. C1 and C4 provide filtering of differential noise and C2 and C3 (along with capacitor C12) filter common mode noise. The noise currents generated by the high speed switching processes in the primary circuit are kept circulating within the power supply rather than allowed to propagate down the A-C powerline.

R1 is used to bleed high voltage from the EMI filter capacitors after the A-C power connection is removed.

The A-C power waveform is rectified by the diode bridge CR1. The bridge is operated as a full bridge rectifier for the 220 VAC input range. In this mode, the rectified voltage on the series capacitor bank C6-C11 is 1.414 × 220 VAC or approximately 310 VDC. Fast-on tabs J2 and J3 are provided to reconfigure the bridge rectifier to a voltage doubler. Plugging in a jumper cable (P1 and P2) causes the center tap of the capacitor bank to be connected directly to A-C neutral. This connection creates a voltage doubler where C6-C11 are charged to peak line voltage on alternate half cycles of the power line. In this connection, only two diodes in the 4 diode bridge are active.

Resistors R5 and R6 are used to allow discharge of the voltage on the capacitor bank, C6-C11 when A-C power is removed. This is a UL and CSA requirement for personnel safety. The resistors also aid in balancing the voltages across the series - parallel capacitor.

As mentioned previously, C12 is noise filter capacitor which is used to keep circulating noise currents in the chassis within the bounds of the power supply and not circulate externally in the power cord.

As explained above, a square wave must be produced on the secondary side of the power transformer, and then the output voltage controlled by use of the synchronous rectifier scheme.

The primary side circuit of the power module (FIG. 4) is the entire half-bridge inverter. The sole function of this subcircuit is to produce a true 50% square wave in the power transformed from the rectified line voltage (approx. 300 VDC).

The power transformed is labelled T6 on the schematic. One primary winding (40 Turns) is used. One side of the primary is connected to the 150 VDC center tap of the C6-C11 capacitor bank via 3 1.0 uF coupling capacitors. For the present, we may consider these capacitors to act as a short circuit at the switching frequencies involved.

The other end of the primary winding is connected to two power MOSFETs, Q9 and Q12.

Q9 and Q12 are driven such that when Q9 is ON, Q12 is OFF and vice-versa. Drive pulses are supplied to Q9 and Q12 via the four small pulse transformers T1 through T4. approx. T1 and T3 provide ON pulses Q9 and Q12 respectively, while T2 and T4 supply the OFF pulses. Supplementary transistors Q7, Q8, Q10 and Q11 are used to aid the turn-off of the main power transistors Q9 and Q12 (see below).

When Q9 is ON, pin 1 of the primary winding is connected to the 300 VDC via the low resistance of the MOSFET. Pin 2 of the primary winding is essentially connected to the 150 VDC tap of the capacitor bank. The capacitor bank values and coupling capacitor values are high enough that the 300V and 150V DC are essentially constant at all times.

Thus, when Q9 is ON, $300-150=+150$ volts is applied across the T2 primary pins 1-2. When Q9 is turned OFF, Q12 is turned ON at the same time. When this occurs, pin 1 of the primary winding is disconnected from the 300V supply and connected to common through the low ON resistance of Q12. Pin 2 is still maintained at 150 VDC, so that the voltage across the primary winding is $0V-150 V=-150V$.

In this way, a square wave with peak values of $+/-$ 150 Volts is produced across the primary winding of the power transformer. The same waveform will exist on the secondary windings, scaled in magnitude by the turns ratio of the various windings on the power transformer.

The half bridge configuration was chosen so that the voltage rating on the power MOSFETS could be kept to 400 VDC. The maximum voltage stress across Q9 or Q12 is equal to the rectified line voltage. With a push-pull type inverter, the effect is to cause a voltage doubling of the line voltage across the OFF MOSFET, requiring expensive 800 or 1000V parts.

The coupling capacitor C33-C35 is used to block DC current. In principle, the average current in the primary winding should be zero when averaged over one cycle of operation. This can be seen by referring back to the diagram for the synchronous rectifier. The MOSFET switches on the secondary side are operated ON and OFF with a 50% duty ratio. They may be phase shifted with respect to the voltage on the transformer secondary, but they are still each on only 50% of the time. If we consider the output filter inductor current to be constant, we can see that the average current in the secondary winding will be zero. So the reflected current in the primary winding, on the average, will be zero.

The inherent mode of operation is such that the average D.C. current through the primary winding is zero. In principle, we should not need coupling capacitor C33-C35. However, the ON times and the OFF times of the inverter transistors Q9, Q11 or the Synchronous rectifier transistors can never be exactly matched. Thus we can only approach a true 50% duty ratio. If the duty ratio applied to the primary of T2 is not exactly 50%, we may have a net positive or negative Volt-sec applied to the primary. A DC magnetizing current will develop in the primary and eventually increase until the core is saturated at maximum positive or negative flux.

The coupling capacitor C33-C35 blocks this DC magnetizing current. If there is an imbalance of the volt-seconds applied to the primary over each half cycle, the resulting increase in DC magnetizing current will charge C33 in such a way as to automatically rebalance the volt-seconds applied to the primary winding. All transformers, high or low freq., must have an average of zero volt-sec on each winding in order to avoid core saturation.

During part of each cycle, energy is returned to the 300V supply by T2 primary current flowing backwards from pin 1 when Q11 is ON or into T2 pin 1 when Q12 is ON. This commutation is allowed by diodes CR22 and CR27. The MOSFETS have an internal parasitic diode that could be used for the same purpose. However, the MOSFET diode is slow with a Trr of about 200 nSec. Thus, when diode of Q9 is conducting and Q12 is switched ON, Q12 will turn on very quickly while the Q9 diode is still not capable of blocking current for about 200 nSec. This condition results in a temporary short circuit between the 300V and Common. This can cause large, damaging currents to flow.

To compensate for the slow parasitic diode in the MOSFET, diodes CR22 and CR26 are added to perform the function. The MUR840 is an ultrafast diode with a Trr of about 30 nSec. To prevent the MOSFET diode from conducting, Schottky diodes CR21 and CR26 are added in series with the MOSFETS. Schottky diodes are used since they have a low forward drop and will not contribute to too much extra heat dissipation.

Current Transformer T5 is used to monitor the primary current in the main power transformer. The 100 turn secondary of T5 is fullwave rectified (CR28-CR31) and fed to scaling resistor R49. The voltage across R49 is fed through voltage divider R47, R48 to the gate of the small-signal SCR Q13. When the gate voltage on Q13 exceeds approx. 0.7 volts, the SCR fires and the converter is turned off for self protection. Since the voltage divider is a factor of 2, then 1.4V across R49 is required to trigger Q13. Since the turns ratio of the current transformer is 100:1, then the threshold current in the primary T6 is $(1.4 V/15 ohm) \times 100=9.33$ Amp. peak. Capacitors C36 and C37 are for noise rejection of noise spikes to reduce nuisance trips.

The primary side control circuits are present for the sole purpose of providing a proper 50% duty ratio, constant frequency drive to the main inverter transistors Q9 and Q12.

The power for the drive circuitry is derived from the rectified line high voltage (300 VDC) initially. Zener diode VR2 is biased to 20V via R10. The 20V is buffered by an emitter follower Q2 and isolation diode CR2. The resulting 18.5 Volt output is held on filter capacitor C13. This voltage is applied to the three terminal regulator U1 to produce a regulated 15 volts for the rest of the control circuitry.

When the converter is turned on by the rest of the control circuitry, a square wave (50 KHz) exists across all windings of the power transformer T6. One winding is full wave rectified by diodes CR3-CR6. The rectified voltage is applied to filter capacitor C13. The winding turns are such that the voltage developed by the T6 winding will be larger than the 18.5V provided by Q2, CR2, even at low input line voltage. Thus, CR2 and Q2 will be cut off, and all power to the control circuits will originate from the T6 winding. This is a low voltage winding. The efficiency of this arrangement is much greater than continuing to use Q2 where the control power would be supplied from 300V.

R12 is used to limit any surge current from the low voltage T6 winding. Also, R11 is used to limit the current and power dissipation in Q2.

The dual comparator U2 in the control circuitry is used to sense the 300V supply and the +15V V1 logic supply voltage. The comparator outputs are diode or'd to form a signal called "RUN". When "RUN" is high, the converter is turned ON. "RUN" will only be asserted high when the 300 Volts supply is greater than 247 VDC and when the V1 supply is greater than 13.0 VDC. Both comparators are configured with some hysteresis to prevent hunting (ON/OFF switching) at the trip point. The reference voltage for the comparators is derived from an independent zener diode, VR1, powered from the 300V supply.

The clock for the converter is CMOS timer chip U3. The chip is configured to oscillated at 100 KHz as soon as the V1 supply exceeds 4 VDC. Following a 100 nSec. time delay (R23-C20) the 100 KHz square wave is applied to flip-flop U4 pin 3. The Q and Q-bar outputs of the flip-flop provide exact 50% duty ratio pulses at 50 KHz.

The two 50 KHz square waves (180 degrees out of phase) are applied to 680 nSec one shots. The One shot circuits are made from the two flip-flops in U5. When the clock input to these flip-flops goes positive, the flipflop is triggered and Q goes high. After a time delay of about 680 nSec created by R26-C23 and R27-C24, the flip-flop resets itself when the reset pin goes high. Thus on U5 pins 12 and 1, we have two waveforms, each a train of 0.68 uSec pulses at 50 KHz with the pulses in each signal staggered by 180 degrees (10 uSec).

Basically, the pulses from U5 pin 13 are used to turn power transistor Q9 OFF and Q12 ON. The pulses from pin 1 are used to turn Q9 ON and Q12 OFF. The NAND gates in U6 are used to gate the ON pulses to the power transistors. ON commands to the power transistors are allowed to propagate to the transistors only when the converter "RUN" signal is high. The OFF pulse to the transistors, however, are always allowed to propagate (safe condition if the transistors are both OFF).

An additional delay of 390 nSec is built in between a power transistor turn OFF pulse and a turn ON pulse. This is done for assurance that (due to turn ON/OFF times) both power transistors Q9 and Q11 are never ON at the same time.

The NAND gates are buffered by the CMOS inverters in U7. The buffers are used to drive the MOSFET low power transistors Q3-Q6 quickly ON and OFF (approx 50 to 100 nSec.).

Q3-Q6 are connected to toroidal pulse transformers T1 through T4. The transformers are used to transfer the ON/OFF pulse commands to the gates of the power MOSFETS Q9, Q12. Transformers are used for signal isolation due to the high voltages on the gate of Q9. The circuitry for Q9 and Q12 must be identical to equalize turn-on and turn-off delays.

When Q3 is turned ON, the full V1 (15V) is applied across the primary of T1. Since T1 has a 1:1 turn ratio, approx. 15 volts appears across the secondary of T1. This voltage is applied to the (capacitive) gate of Q9 via limiting resistor R37. When the gate of Q9 is charged to about 4 volts, the MOSFET starts to turn ON. High charging current (1 to 1.5A) is required to be supplied to the gate to turn the MOSFET on within 100 nSec. This is necessary to minimize switching loss in the transistor. The pulse of 680 nSec is all that is necessary to turn ON the gate of Q9. The gate charge will remain to keep the transistor ON since the gate charge is prevented from bleeding away by diode CR19.

When transistor Q4 is turned on (10 uSec later for 680 nSec) a 15V pulse appears on the secondary of pulse transformer T2. This pulse turns ON low power MOSFET Q8. This transistor turns on very quickly and discharges the gate of power transistor Q9 through the 10 ohm resistors R37 and R38 and Q9 is turned OFF. The pulse lasts for 680 nSec. However, the gate of Q9 must be kept off. Charge may get into the gate by leakage or injection through the "Miller" capacitance between Drain and Gate. Thus C30 is provided to hold the gate of Q8 ON so the Q9 may be held OFF.

When Q9 must be turned ON again, the Secondary of T1 must provide gate charge to the gate of Q9 as explained above. In addition, transistor Q8 must be simultaneously turned OFF to avoid shorting T1 and preventing Q9 turn-on. The T1 secondary also drives bipolar transistor Q7 ON to discharge the gate of Q8 and turn it OFF.

The same process of turn-on and turn-off occur in Q12.

The net result is that Q9 and Q12 are alternately turned ON and OFF and there is a period of about 200 nSec between alterations where both transistors are OFF. During this simultaneous OFF time, the power transformer T6 primary current is carried by the commutation diodes CR22 or CR27 (depending on the direction of the primary current at the time).

The basic 100 KHz clock signal is also routed from the clock oscillator another 680 nSec one shot made up of one of the D flip-flops of U4. The output of the one shot is buffered by the parallel connected CMOS inverters of U7. The buffers drive the pulse transformer T7 with a 680 nSec pulse which is transferred to the secondary side of the converter.

Figure 5A:
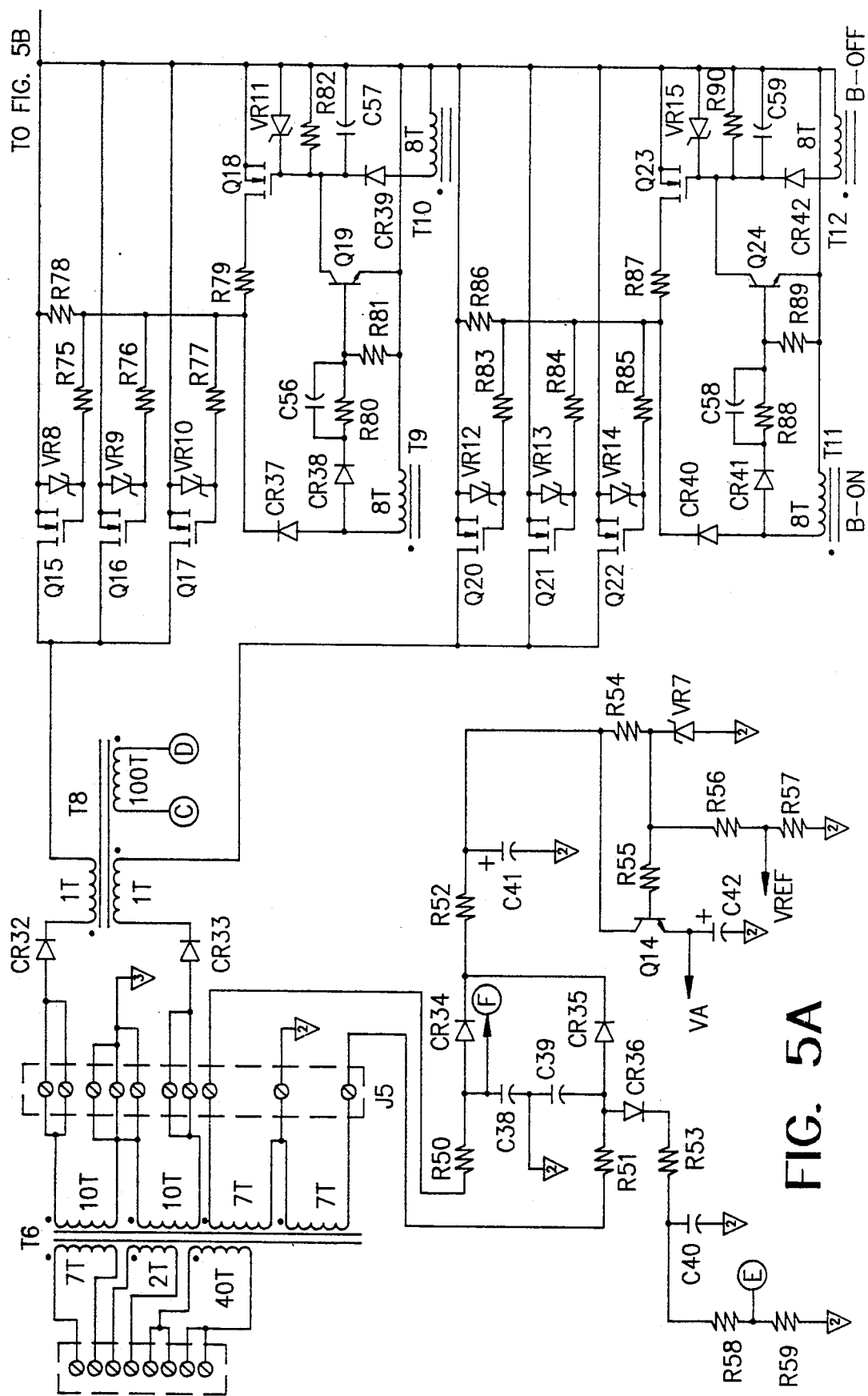
Figure 5B:
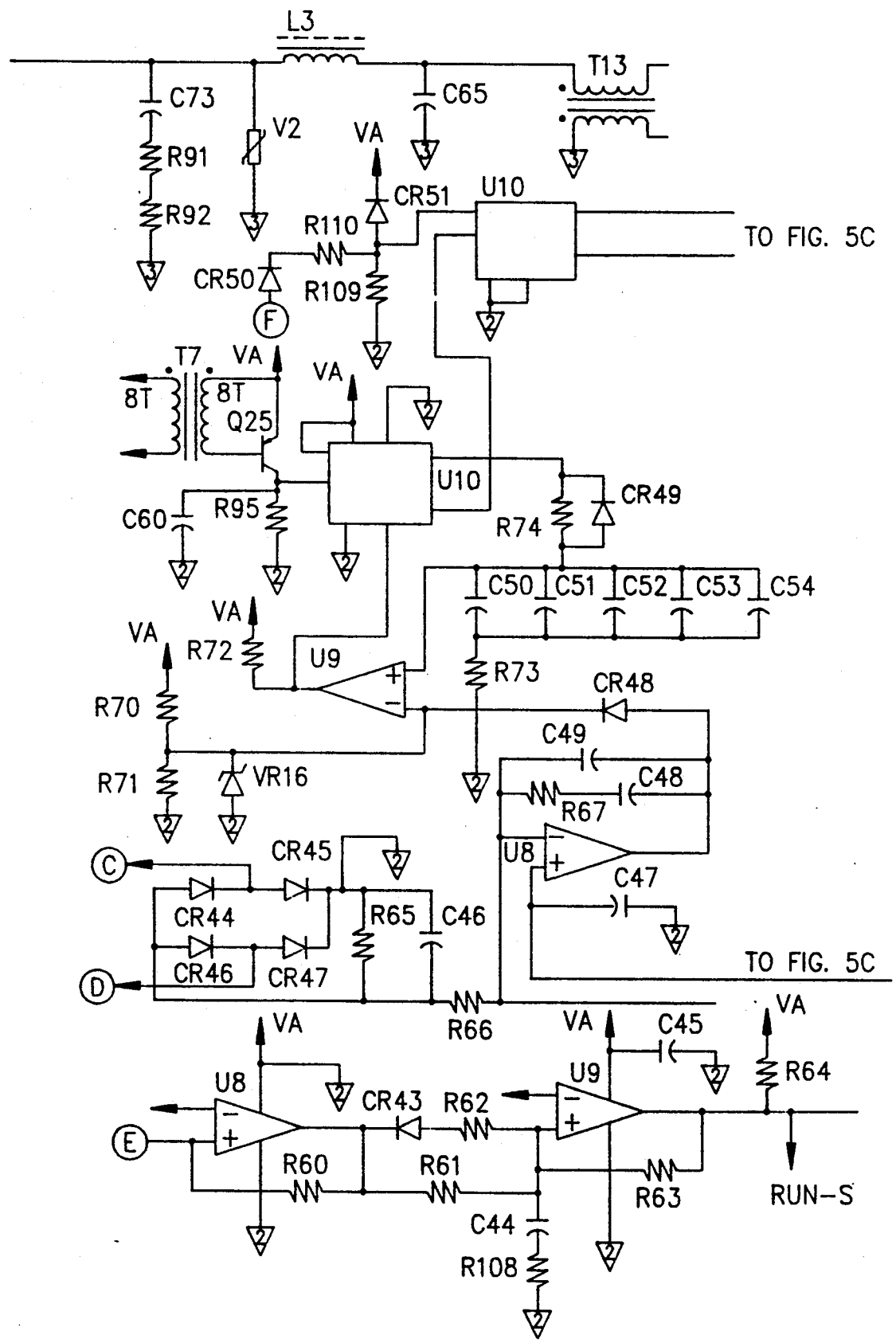
Figure 5C:
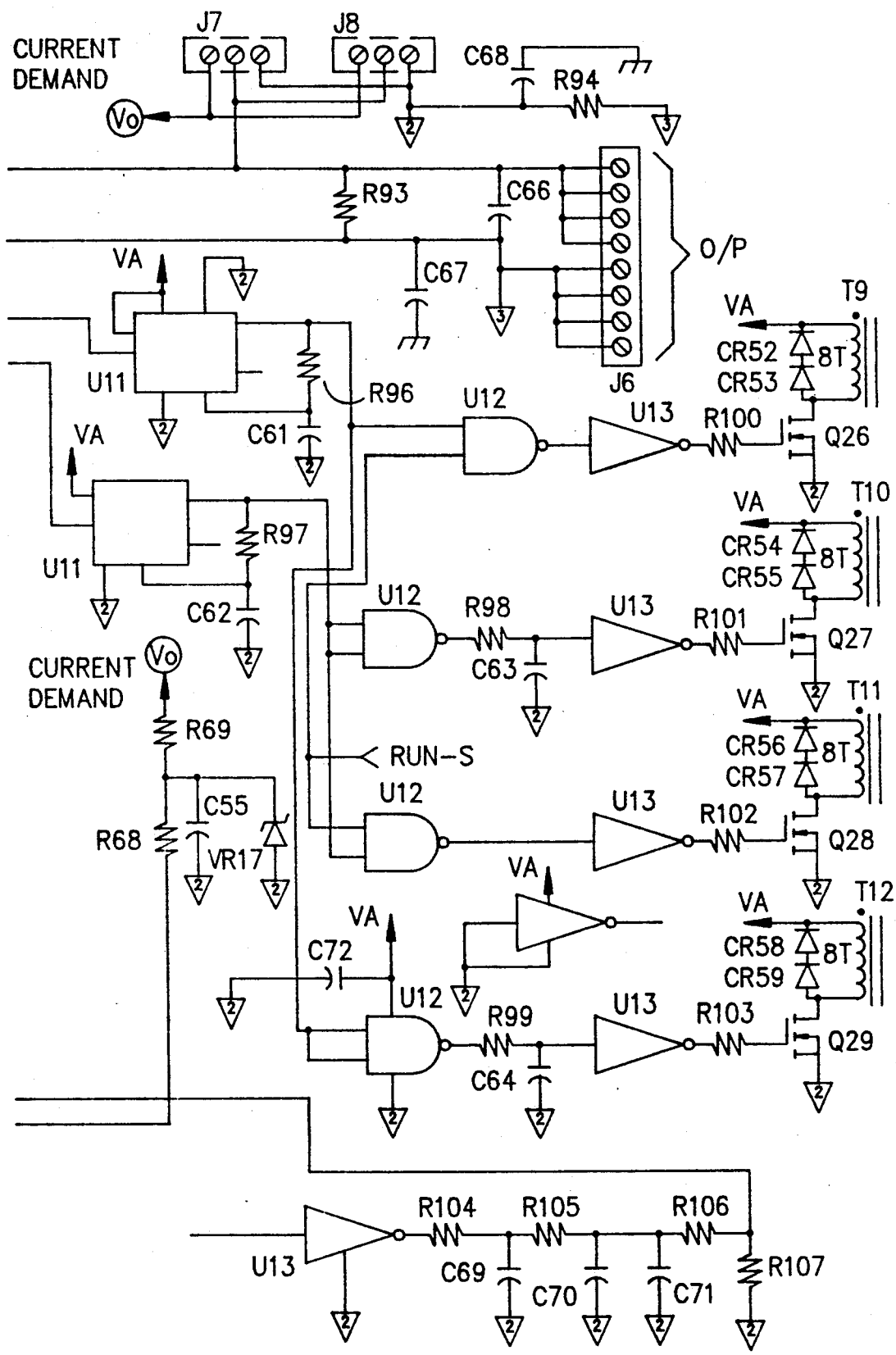

Referring now to FIGS. 5A-5C, the two square waves from the high frequency inverter transformer appear on the secondary windings of T6. The high current outputs are the two 10 turn windings. The two 7 turn windings are used to develop house-keeping power for the secondary side control circuitry.

The square wave amplitude on the 7T windings is 26V nominal, varying with the rectified line voltage. The windings are series connected to form a center tap output winding. The center tap is referred to the local common "2". The voltage on the windings is full wave rectified and filtered by R52 and C41 to provide an unregulated D.C. supply. Resistors R50, R51 and capacitors C38 and C39 form a noise snubbing network on the power transformer secondary. The raw D.C. is regulated to approximately 14.2 V by the zener diode VR7 and transistor Q14.

A 7.5 reference voltage is also developed from the zener VR7.

The voltage on the 7T windings is also monitored by filter capacitor C40. CR36 and C40 form a peak detector. The discharge time constant is short enough that the amplitude of the winding voltage can be followed with only a two millisecond delay. This voltage is divided down by the R58, R50 divider as a scaled representation of the input rectified line voltage.

The synchronous MOSFET power transistors are two sets of paralleled MOSFETS. Q15, Q16 and Q17 are paralleled as one composite transistor as are Q20, Q21 and Q22. The MOSFETs are parallel to obtain a low composite ON resistance. Since the MOSFETs will be carrying the entire output current (up to 25 amps) a low ON resistance is essential to low losses.

The drive scheme for the synchronous detector MOSFETs is identical to that of the primary side power MOSFETs Q9 and Q12. The drive method has been explained above in &:he discussion of the primary-side control circuitry.

The object of the secondary-side control circuit is to adjust the phase delay between the drive waveforms for the primary side power MOSFETs and the secondary side synchronous detector power MOSFETs. The phase delay will determine the output voltage. The output voltage is adjusted to maintain a commanded output D.C. current level.

The secondary-side control circuit obtains a synchronization pulse from the pulse transformer T7. T7 is driven with a series of 680 nSec pulses at the clock frequency. These pulses are used to reconstruct the primary side drive waveforms with a controlled phase delay.

The pulse from the pulse transformer is amplified by the PNP transistor Q25. A series of positive pulses at 100 KHz appears across resistor R95. These pulses are used to clock the flip-flop U10 pin 3. The flip-flop is configured as a one shot timer. The D input is permanently connected to logic high. When a positive going pulse appears on U10 - pin 3 the Q output goes high (U10 - pin 1), The capacitors C50 through C54 are charged through R74 to produce a voltage ramp to the positive input of comparator U9 pin 5. Resistor R73 is used to add a pedestal to the ramp waveform on the capacitors. The capacitors are parallel since it is easier to obtain NPO, 2% capacitors of 100 pF rather than 470 pF.

A voltage from the control loop error amplifier (U8 - pin 7) is applied to the other input to comparator U9-pin 6. When the ramp voltage on the U9 - pin 5 exceeds the voltage output of the error amplifier, U9 pin 7 goes high. This high is applied to the reset pin (U10 - pin 4) of the flip-flop. The Q output (U10 - pin 1) is forced to zero and the Q-bar output (U10 - pin 2) is forced high. This results in two further events: the capacitors C50 to C54 are quickly discharged through CR49 and R73 to reset the ramp for the next cycle; and the flip-flop U10 - pin 11 is clocked.

The clock pulse to U10 - pin 11 is essentially the pulse from T7 delayed by the time delay required for the ramp waveform to trigger the comparator U9 - pins 5, 6 and 7. This time delay is controlled by the output of the control loop error amplifier.

The (controlled delay) 100 KHz pulse train applied to the clock input U10 - pin 11 is divided by two by the flip-flop. At U10 pins 13 and 12, there are two 50 KHz square waves of exactly 50% duty ratio and the square waves are 180 degrees out of phase. The transition edges in the waveforms are delayed from the voltage waveform appearing on the secondary of power transformer T6 by the amount of delay controlled by the control loop error amplifier.

These two phase shifter waveforms are fed to dual flip-flop IC U11. Both halves of the dual D flip-flop are connected as one shot timers. The duration of the one-shot pulse is set by the R-C time constant of R96-C61 and R97-C62. These are both 680 nSec. The pulses are used to turn the power MOSFETS on and off in exactly the same manner as the primary power MOSFET drive scheme. One difference is that on the secondary side, three MOSFETS are connected in parallel to obtain a reduction in the composite ON resistance to reduce power dissipation losses.

Another significant difference in the drive scheme is that the time delays in the ON and OFF pulses to the MOSFETS are arranged such that the secondary side power MOSFETS overlap in conduction by 100 or 200 nSec. This would appear to cause a short across the secondary of the power transformer T6. However, power diodes CR32 and CR33 prevent short circuits across the transformer secondary even if both banks of power MOSFETS are ON. Contrast this to the situation on the primary where a conduction overlap in the power MOSFET transistors would be disastrous due to unlimited currents flowing. On the secondary side, the sum of currents through CR32 and CR33 is always equal to the output inductor L3, current. This is true whether both banks of MOSFETS are ON at the same time or not.

Conduction overlap is built in to avoid another type of disaster which occurs if both banks of MOSFETS are OFF at the same time. The ideal case is that MOSFETs Q15–Q17 turn CFF exactly at the instants that MOSFETs Q20–Q22 turn ON. This is impossible to achieve in practice. If both banks of MOSFETs are OFF, then there is no explicit path for the L3 output inductor to flow through. The inductor will make a path by creating a large back EMF to break down the MOSFETS into conduction. This will cause destruction of the MOSFETS.

In low output current applications, an R-C snubber could be placed across L3 and common to provide a path for L3 current to flow during the time both MOSFETs are OFF.

Overlapping conduction positively ensures that there is always an L3 conduction path through the MOSFETs and power transformer T6. This eliminates the requirement for power consuming snubbers.

A small amount of snubbing is provided by C73, R91 and R92. This is used to dissipate energy ringing in parasitic L-C tank circuits formed by the L3 inductor and parasitic capacitances in the power MOSFETs and physical layout.

An internal varistor, V2, is installed to provide a path for L3 inductor current to flow and dissipate stored energy in the inductor in the case where the power MOSFETs are turned OFF while L3 current is still flowing.

The control loop is based on an input signal which commands a given level of output current, a current transformer which feeds back a signal proportional to output current, and an error amplifier to measure the difference. The output current is the L3 inductor current. L3 current is essentially constant with a small triangular ripple component. This constant inductor current is supplied by either CR32 or CR33, depending on which bank of power MOSFETs is ON. The pulsating current through the power diodes is monitored with a current transformer T8. In order to avoid saturating the current transformer, CR32 is connected to a 1 turn winding at a start, while CR33 is connected to one turn winding at a finish. Since the magnitude of the CR32, CR33 currents are equal are both exactly 50% duty ratio, the average volt second into the T8 windings is zero, thus preventing saturation of the transformer.

The 100 T secondary of the transformer is full wave rectified and a voltage proportional to the L3 current is developed across R65. The current feedback is presented to the error amplifier U8 - pin 6 through the scaling resistor R66. A current demand signal, Vd, is fed to the error amplifier through R69 and R68. The error amplifier is used to amplify the difference between the demand and the feed back signal. The output of the error amplifier is fed to the phase delay circuitry as described above to control the output voltage and hence, the output current.

R67, C49 and C48 are compensation networks to roll off the error amplifier for control loop stability.

To examine the relationship between current demand and output current, we show some simple relationships. The output current (L3 current) is sampled by current transformer T8. Since the turns ratio is 100:1, the transformed current into R65 is Io/100. Thus, the voltage across R65 is [(Io/100) × 3.92 ohms] / 1.0 k=Vd / (9.1 k +0.91k).

Solving this equation yields the result that Io = 2.55 × Vd. Thus, a full scale value of Vd=10 volts will command a full scale output current, Io, of about 25.5 amps.

VR17 is used to limit the level of current demand to about 27 amps.

The other components in the secondary side control circuit are used to control the manner of start-up of the circuit. A scaled version of the input line voltage is derived from the power transformer, T6, turns ratio and the resistive divider R58 and R59. This voltage is compared to a 7.5 voltage reference signal derived from VR7. When sufficient input line voltage is present, the output is enabled and the power MOSFETs are turned ON and OFF to allow power transfer to the output. When the voltage on R59 exceeds 7.5 volts, comparator U8 - pins 1, 2 and 3 go high. The pin 1 output is applied to a R-C time delay consisting of R61 and C44. This time delay is about 220 mSec. At the end of this period, the comparator U9 - pins 2, 3 and 1 go high. This output is termed "RUN-S" for the secondary side run command. This signal is used to gate the power MOSFETs ON, enabling power transfer.

The "RUN-S" signal is also applied to a time delay circuit consisting of U3 - pins 11 and 12, R104–R107, C69 –C71 and diode CR60. When "RUN-S" is low, the non-inverting input to the error amplifier is held high (U8-pin 5). This forces the output of U8 - pin 7 high which commands maximum delay from the phase shift control circuit. This will command minimum output voltage and current. When "RUN-S" goes high, indicating that the converter is running on the secondary side, U8 - pin 5 is allowed to discharge towards common. This allows the error amplifier to slowly ramp down from maximum output voltage to normal. This technique implements a soft-start where output current is ramped up from zero to full commanded value at turn on. This is done to reduce high current transients that may overstress components during startup.

Capacitor C65 is used to provide noise filtering. T13 is a common mode choke to attenuate common mode output noise. C66 and C67 are also used for high frequency noise filtering.

R93 is a bleed resistor to discharge C65 and power turn-off.

Clipping network CR50, CR51, R110 and R109 are used to synchronize the regenerated and delayed drive waveform with the proper half cycle from the secondary of the power transformer.

Figure 6:
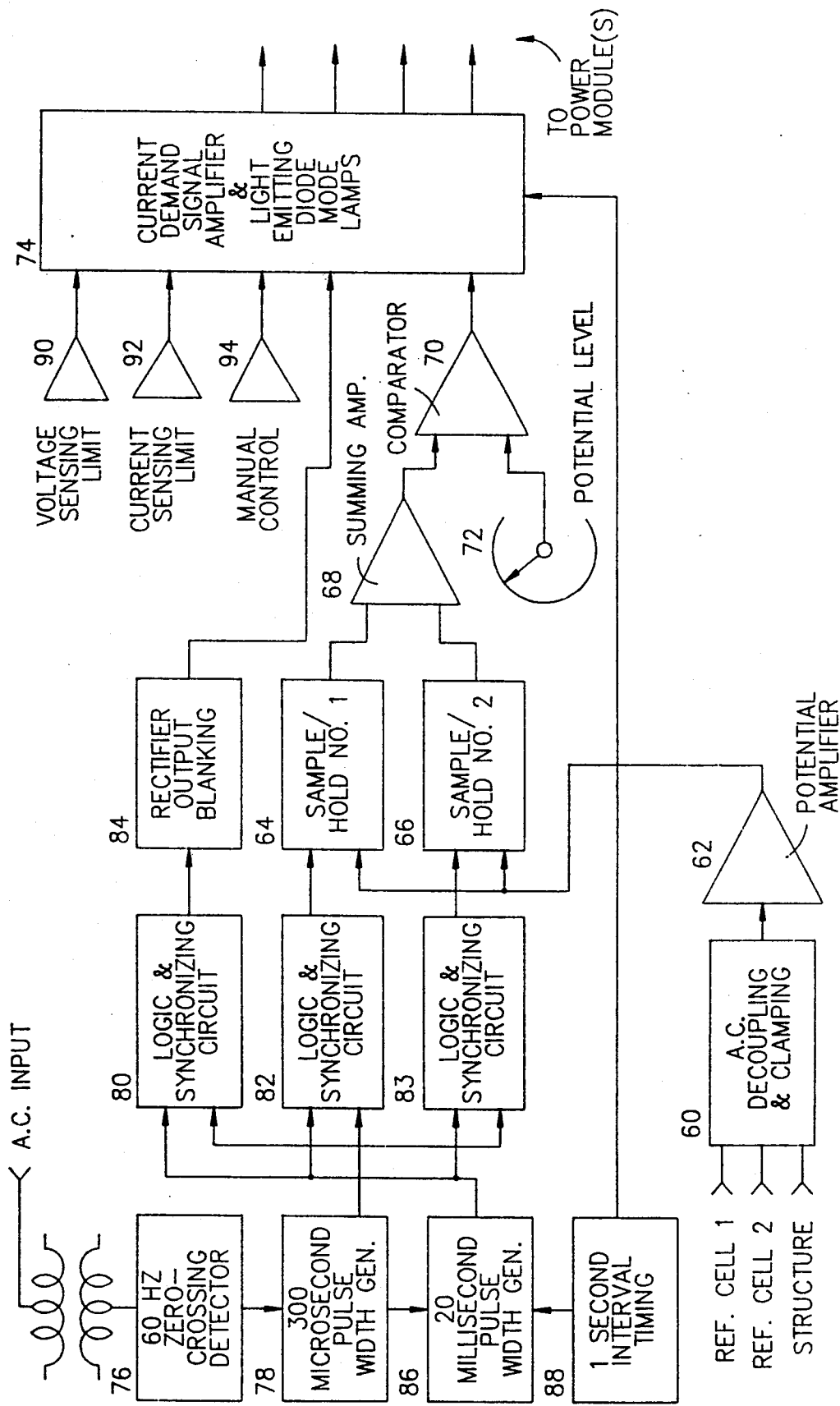
FIGS. 6 is a block diagram of an analog control feature of an alternative embodiment of the subject invention, and FIGS. 7A-7C and 8A-8C comprise detailed schematics of the analog control shown in FIG. 6.
Figure 7A:
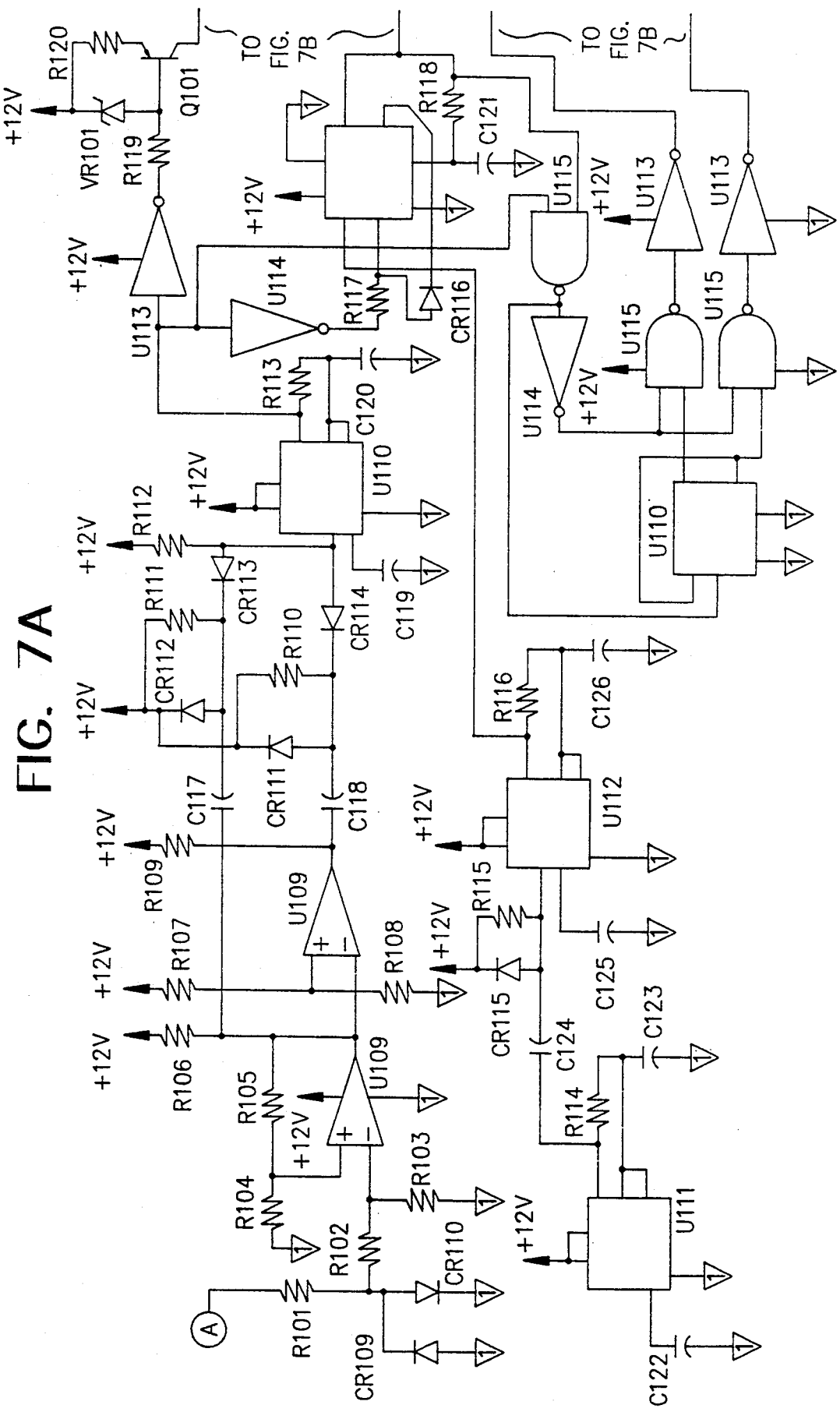
Figure 7B:
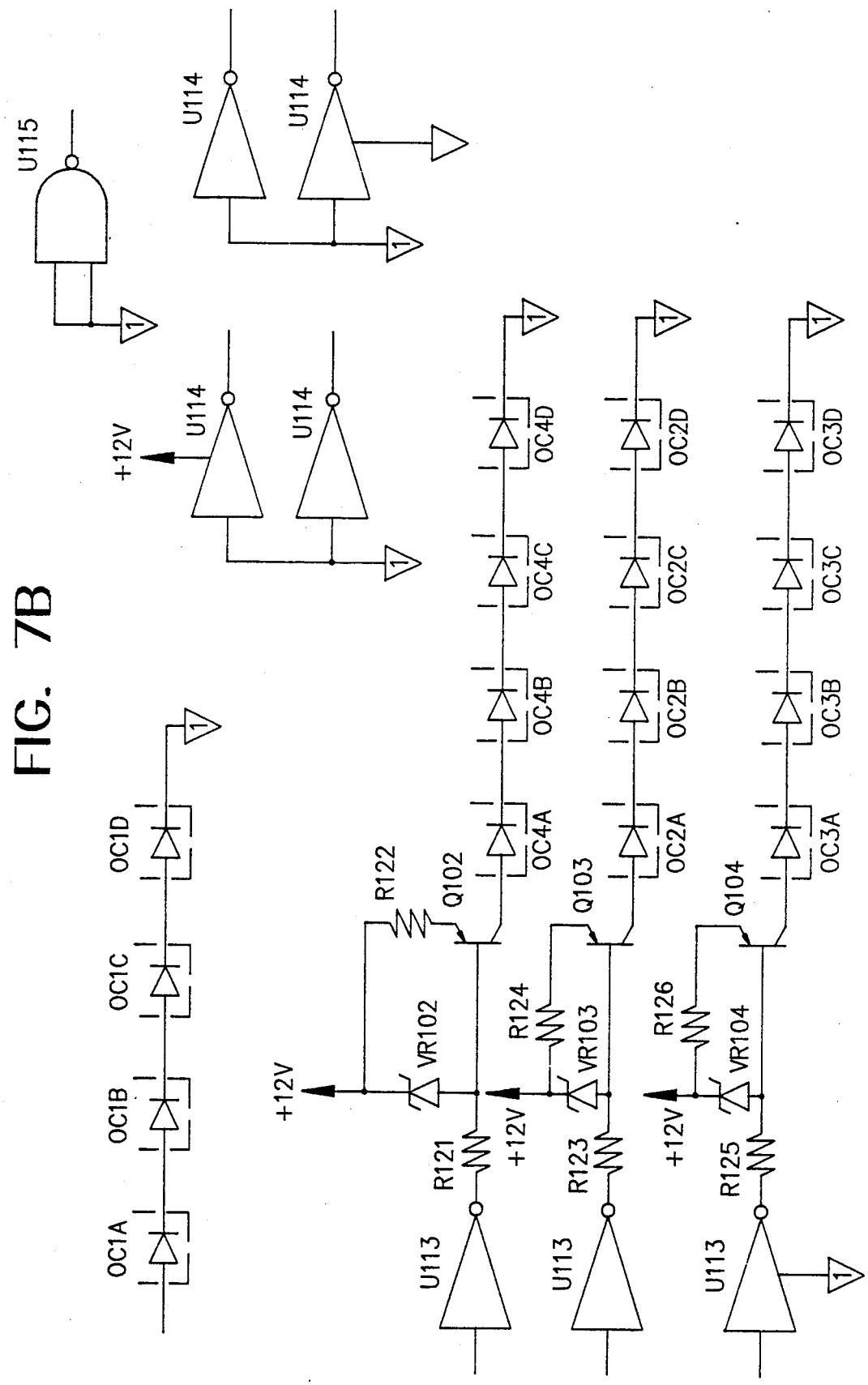
Figure 7C:
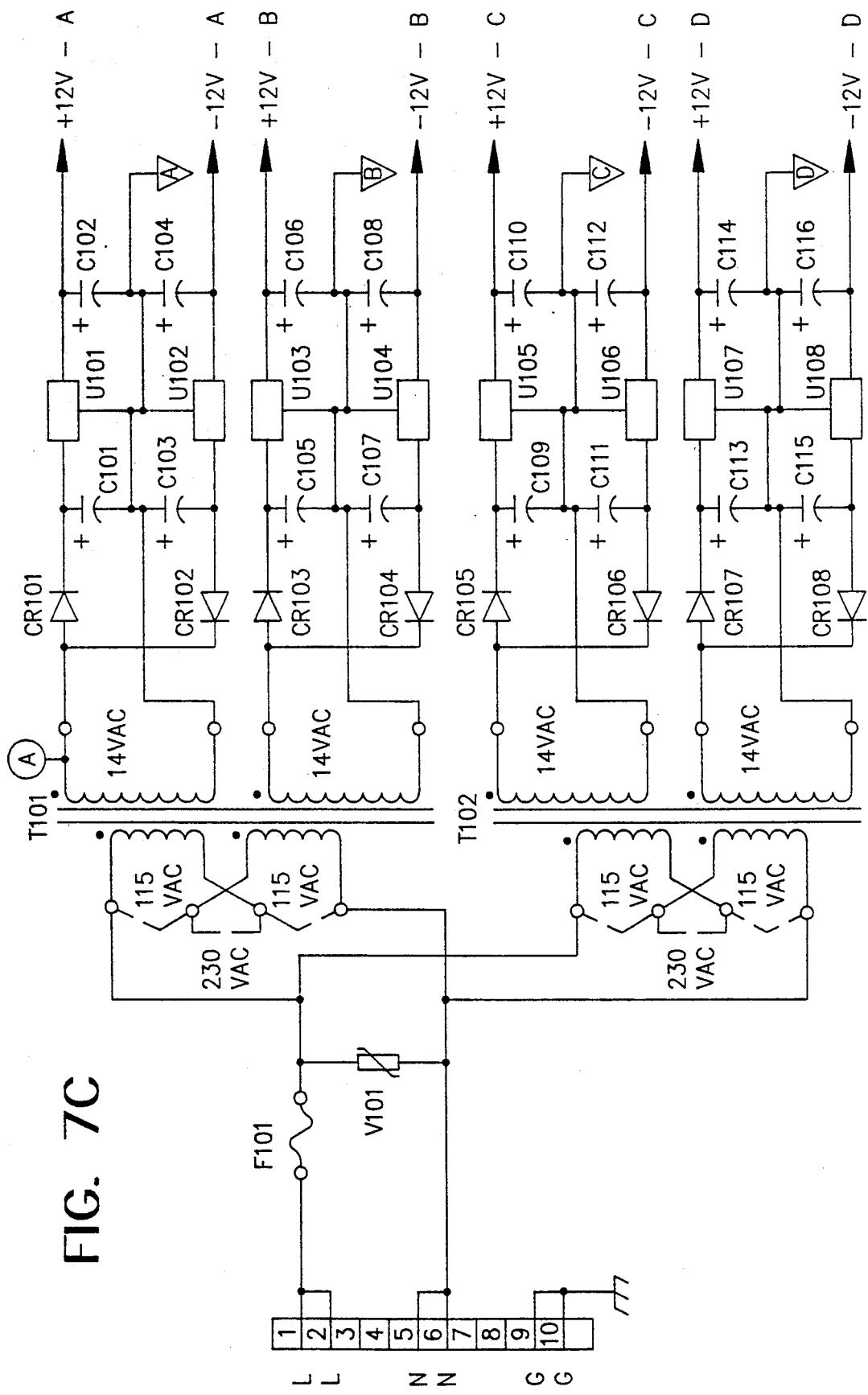
Figure 8A:
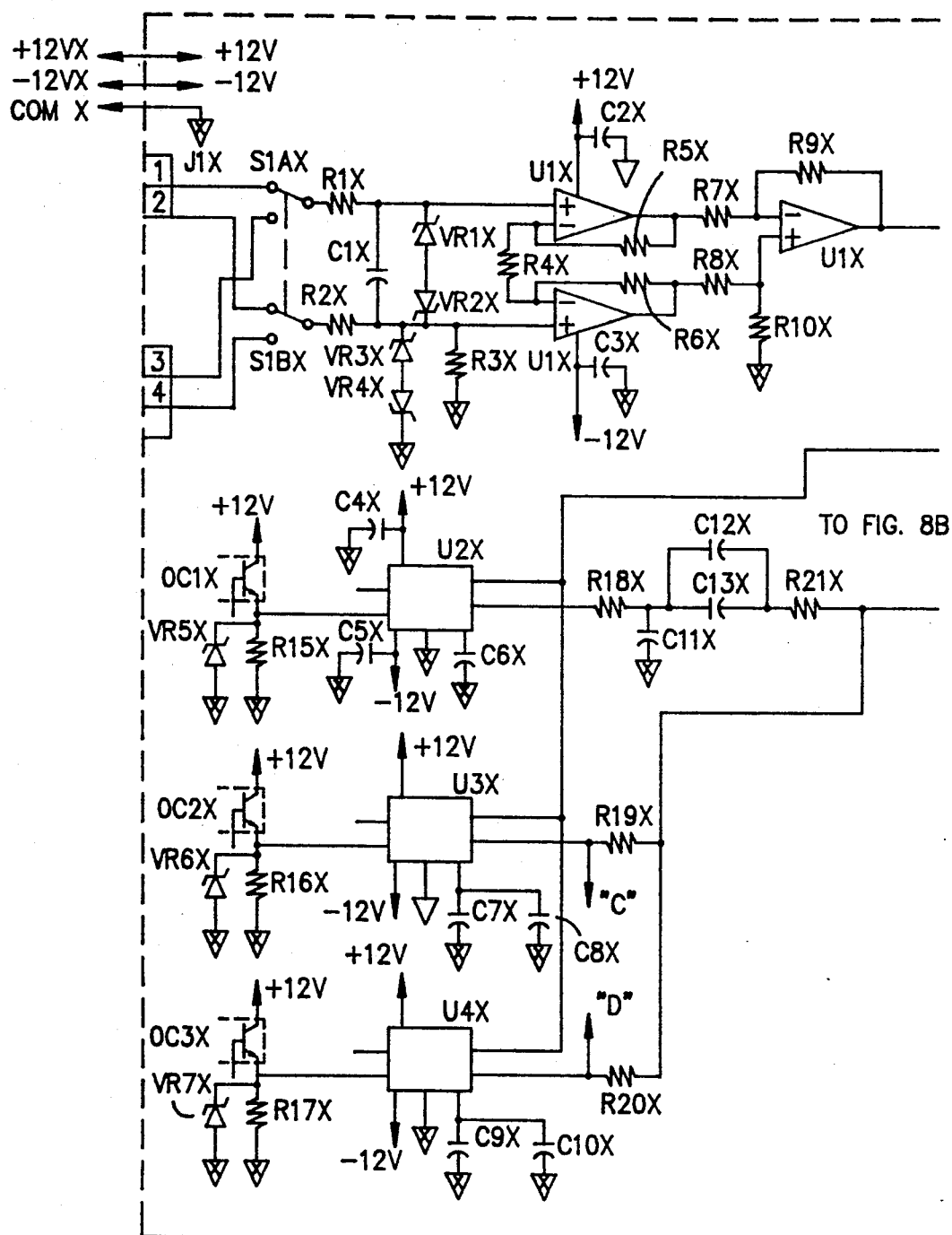
Figure 8B:
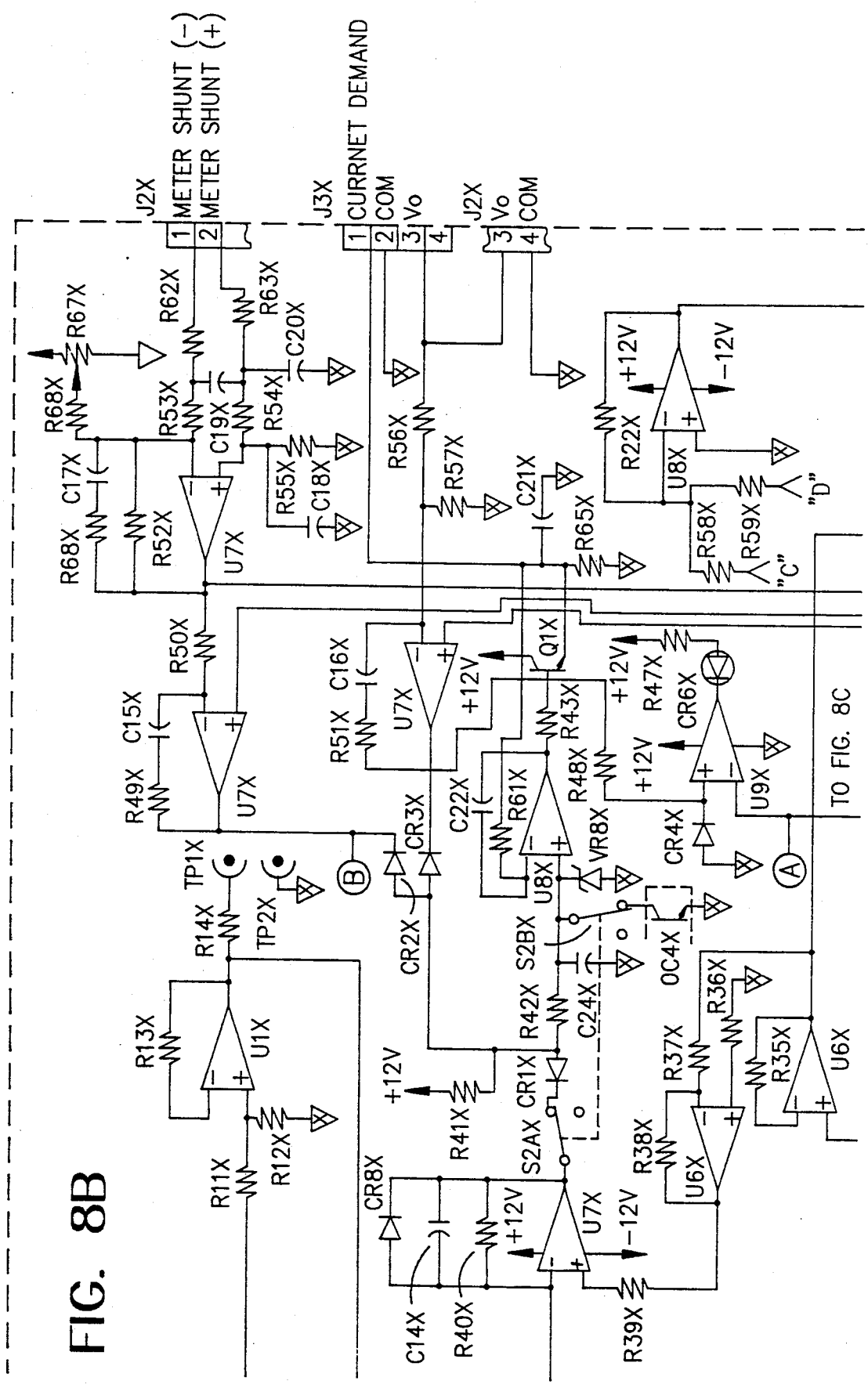
Figure 8C:
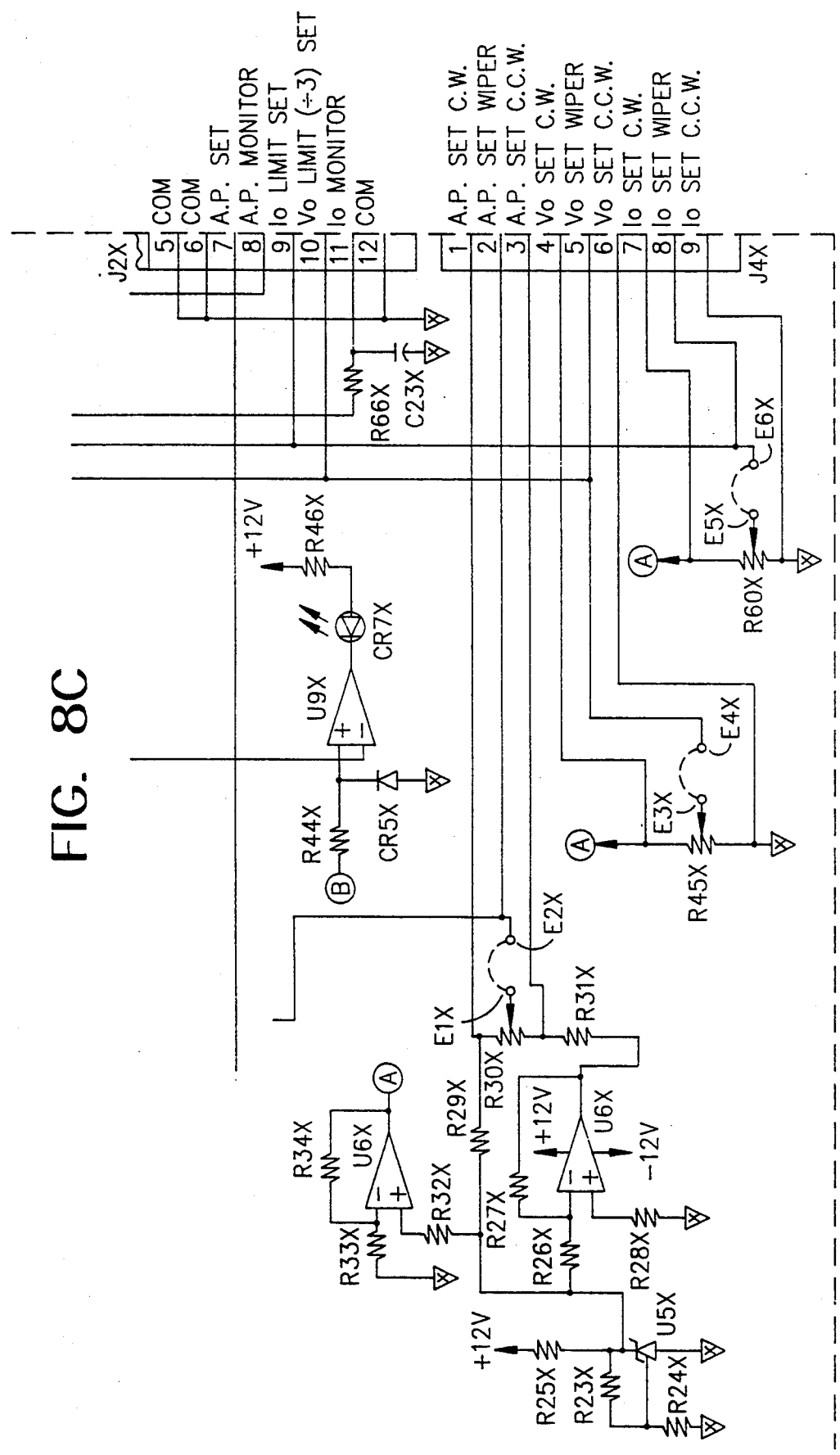

With reference to FIG. 6, a block diagram of the analog control circuit is shown. It is a representation of an alternative embodiment of the subject invention. The circuit is powered by a commercially available power source. The FIGURE will be described with reference to the present invention being in the "auto-potential" mode.

FIG. 9 shows an application of the invention having the analog control circuit that is particularly useful for off-potential measurement that is I-R drop free and automatic adjustment of the impressed energy level to the structure. The inventors refer to this feature as "auto-potential" mode. The controller 100 senses the potential difference between the structure 102 and a reference cell 104 during a period of time when the supply of output energy is selectively halted. Due to the use of the subject switch mode power circuit and synchronous detector switch assembly, the output filter will not offset the measurement so that the measurement is I-R drop free from improved system accuracy. The measured potential is compared with a preselected desired potential level and the supplied energy is adjusted in a preselected scanner for improved cathodic protection and anode use efficiency.

As can be seen in the lower left-hand corner of FIG. 6, a connection from the reference cell electrode and an other connection from the structure to be protected are connected to the circuit at 60, for A.C. decoupling and clamping. The signals are passed on to a potential amplifier 62 where the voltage between these two connections is measured to determine the structure barrier current is turned off, thereby allowing sampling from the reference cell and the structure, two voltage control measurements of the off potential are taken. The measurements are taken at the next two zero crossing points of the local A.C. utility line. The first measurement being stored in the sample hold circuit 1 64 and the second measurement being stored in the sample hold circuit 2 66. These two measurements are then passed to the summing amplifier 68 where the average of the signals from 64 and 66 is determined. Two measurements are taken on the alternate zero crossing of the A.C. input in order to discriminate against power line frequency and related noise currents which might otherwise cause distorted readings. The average value of the measured off potential from the structure is applied to one input of comparator 70. The second input of comparator 70 receives a signal from the precision potentiometer 72, which set point preset value may be adjusted to select the desired auto potential to be maintained by the control system. The output of comparator 70 is then sent to a current demand signal amplifier 74 which passes the value received from comparator 70 to the power modules where it is used to alter the output voltage.

The sampling scheme described immediately above occurs once every second. The signal to start the sampling scheme occurs when the 60 Hz zero crossing detector 76 senses the A.C. signal crossing zero. The sensing by detector 76 causes a 300 microsecond pulse to be generated from a 300 microsecond pulse width generator 78. This pulse is transferred to logic synchronizing circuits 80, 82, and 83. The signal from logic synchronizing circuit 80 is passed to the rectifier output blanking circuit 84, which is used to signal the controller to turn off the power supply output. The signal lasts for 20 mSec. and during this time the output current for the power supply is turned off. This pulse occurs once every second. The 300 microsecond pulse from the generator 78 is also passed to a 20mSec. pulse width generator 86 which is used to signal the controller to sample the voltage between the steel structure and the reference cell. This pulse occurs twice during the 20 mSec. off period, at the first two consecutive A.C. zero crossings. A one second interval timing block 88 signals the beginning and end of each timing scheme. The voltage sensing limit 90, the current sensing limit 92, and manual control 94 set the upper and lower limits of the circuits operating capability.

The circuit is designed to control up to four independent channels of cathodic protection power supplies. Since the power module output commons may be referenced to different points, and a controller channel output must be referenced to its associated power module, all four controller channels must be floating.

Thus the circuitry of each of the four identical channels is powered independently from an isolated winding of a 60 Hz stepdown transformer.

A controller channel may be operated in any one of three modes, constant voltage, constant current or auto potential.

With reference to FIGS. 7A-7C and 8A-8C, a detailed schematic of an embodiment of the analog controller is shown.

The input power is 120 VAC or 220 VAC single phase, 60 Hz utility power. The AC is applied to a terminal strip input connector. A fuse, F101, is installed for safety. A 250 VAC varistor, V101, is used to provide limited protection for line surges and voltage spikes due to lightning.

Two 60 Hz low power step-down transformers are used to step down the AC input voltage to about 14 VAC. The transformers are of the dual primary type. The primary windings may be connected in parallel for operation at 120 VAC, or in series for operation at 220 VAC. The strapping arrangement is shown on the schematic. A commercial line changer switch designed for this purpose may also be used to configure the AC input to the controller.

Each transformer has two separate low voltage secondary windings. With two transformers, a total of four isolated windings are available which are used to crate four isolated power supplies. A separate supply is used for each channel to allow each channel to be referenced to independent reference points in the system.

Each transformer secondary is followed by a conventional rectifier/capacitor voltage doubler. For each channel, a raw $+/-18$ Volt supply is created by the doubler circuit. The raw DC is regulated down to two $+/-12$ Volt output by use of a positive and negative three terminal voltage regulator.

The power for channel A is slightly different in that the channel A power supply is used to power the timing and strobe circuitry common to all four channels. The timing and control circuitry is galvanically isolated from channels B, C, and D by optoisolators, thus preserving total channel to channel isolation.

The timing and strobe circuitry is located on the bottom half of FIG. 7.

The purpose of the timing circuit is the coordination of the power supply turn-off, Off Potential sampling instants, and power supply turn-on, with the zero crossing instants of the AC utility voltage.

The timing circuit is operational at all times, but the timing signals are only really required by those channels set for autopotential mode.

The timing and strobe circuit has four outputs: S/H #1, 2, and 3 and Io Blank. These outputs are short duration current pulses each applied to four optoisolator diodes connected in series. There is one optoisolator for each signal for each channel to distribute the four timing signals to each of four channels in a completely isolated manner.

As mentioned previously, the timing and strobe circuits are powered from the channel A power supply. This places a higher output load on the Ch. A supply.

One end of the transformer secondary associated with the Ch. A power supply is connected to R101. The waveform is a scaled down version of the utility line voltage. R101 is used to limit the current from the transformer secondary to the two clipping diodes CR109 and CR110. The voltage across this diode pair will be $+0.7V$ on the positive half-cycle of the 60 Hz AC voltage on the transformer secondary, and $-0.7V$ on the negative half. The diodes are used to limit the input voltage to the comparator U109-pin2. Resistors R102 and R103 are used to provide a leakage current path for the diodes and the comparator input as well as form a voltage divider. This prevents the input to the comparator from going below $-0.35V$ for safety. The comparator is also provided with hysteresis from positive feedback via resistors R105 and R104.

When the AC line voltage approaches the zero voltage crossing point, the voltage across the clipper diodes will swing from $+0.7V$ to $-0.7V$ or vice-versa. Near the point where the voltage is zero, the comparator will change state. The hysteresis is provided to prevent multiple ON/OFF comparator pulses at the zero crossover point.

The output of the comparator is presented to a second comparator which is used as a signal invertor. U109-pin5 is biased at half the supply voltage. When the comparator output U109-pin1 switches, it will swing from 0 V to $+12V$ or vice-versa.

Thus the voltage waveforms existing on U109 pins 1 and 7 are two square waves with 50% duty ration, 60 Hz period, 180 degrees out of phase with the transition edges co-incident with the zero crossing instant of the 60 Hz utility line.

The two square waves are applied through small 330 pF coupling capacitors C117, C118 to the trigger of U110, a CMOS timer. When the trigger pin (U110-pin2) is pulled below 3 volts momentarily, the timer is triggered. The timer is configured as a one-shot and R113 and C120 are selected to give a timer pulse width of about 200 microseconds.

Since the timer is triggered by the negative edge of either of the two square waves from the U109 comparator, the output of the timer U110 is a continuous wavetrain of 200 uSec pulses with a pulse repetition rate of 120 Hz. Furthermore, the RISING EDGE of the 200 uSec pulses occur at the zero crossing instant of the AC power line.

The output of timer U110 is applied to CMOS buffer invertor U113-pin3. When a 200 uSec positive pulse is output from the timer, U113-pin2 goes low. This drives the PNP transistor Q101 ON. Q101 is configured as a constant current source. Zener diode VR101 is connected from the $+12V$ to the base of Q101. Thus when U113-pin goes low, the base voltage is limited to $12V-5.6V=6.4V$. Thus, the voltage across current limiting resistor R120 is limited to $12V - (6.4 + Vbe)$. Since Vbe for the transistor is about 0.6V, the voltage across R120 is limited to 5.0V. Thus, the emitter current is limited to 5 mA. Since the transistor is operated in its linear region, the collector current will also be 5 mA.

Thus, a 200 uSec, 5 mA pulse is applied to the series string of optoisolator input diodes. The diode drops are about 1.5V per diode, for a total drop of 6V when the current pulse is on. Thus, the transistor is kept in the linear region. The diodes are used to distribute optoisolated, 200 uSec timing pulses to each of the four channels. The drive scheme of all the other optoisolators to distribute timing signals is identical to that described above for transistor Q101. The other drive transistors are Q102, Q103 and Q104.

The timing signals are used as follows:

Io Blank is used to signal the controller to turn off the power supply output. All four channels receive this signal simultaneously. The signal lasts for 20 milliseconds and is the time the output current for the power supply, of each channel is turned off. It is during this 20 mSec period that the measurement of the Off Potential is performed. The Io Blank pulse occurs once very second.

S/H #1 is used to signal all four controllers to sample the voltage between the steel structure and the reference cell. This pulse occurs only once during the 20 mSec Io Blanking period and it occurs at the first AC zero crossing instant following the initiation of the Io Blanking pulse command. Pulse=200 u Sec.

S/H #2 is used in the same manner as S/H #1, except, that it occurs at the second AC zero crossing instant following initiation of the Io Blanking pulse command.

S/H #3 is used to signal all four controllers to sample the voltage between the steel structure and the reference cell. This pulse occurs at every AC zero crossing instant and the voltage sampled is the On Potential of the barrier. This sampling is optional and is used to monitor the rate of change of the On Potential in future applications that may require faster loop response than the present configuration.

Since we are sampling the Off Potential once every second in order to control the Off Potential, we have sampled data control system. Inherent in this sampling process are phase delays. For a one second sampling period, the overall control loop will have 180 degrees of phase shift at approximately 0.5 Hz. Thus, we must keep the open loop gain of the overall control loop less than 1 at frequencies below 0.5 Hz. In fact, we must roll off the control loop gain considerably to achieve a stable system. The closed loop response time of the controller is on the order of 10 seconds which is more than fast enough for corrosion protection applications.

In any future applications requiring faster response, the autopotential (even though is an On Potential) is sampled at 120 Hz to provide an 8.33 mSec period between output samples rather than the current 1 Sec period. The Off Potential will still be controlled, but the rate of change of the On Potential may be fed to the controller via S/H #3.

The 200 uSec, 120 Hz pulse train from timer U110 is also applied to buffer U114-pin3. The invertor output, U114-pin2 is applied to the clock input of the D flip-flop U116-pin3. This flip-flop clock is active on the rising edge of the clock input. Thus, the flip-flop is clocked at the END of the 200 uSec pulse from the timer U110. Normally, a logic zero is present on the D input pin, U116-pin5. This results in a zero being continually clocked into the flip-flop, leaving the Q output, U116-pin1 in the logic low state. When U116-pin1 is low, U113-pin4 is high, which keeps transistor current source Z102 off. Thus, the Io Blanking is inactive.

U111 is a CMOS timer, configured as a 1 Hz oscillator. On the falling edge of the square wave from U111-pin3, a logic low pulse is AC coupled to the trigger pin of another CMOS Timer IC, U112. When U112-pin2 is pulled low momentarily, U112 is triggered. U112 is configured as a one shot, 12 millisecond timer.

Thus, approximately once per second, U112 puts out a single 12 millisecond pulse. This pulse is applied to the input of the D flip-flop, U115-pin5. Since there is a clock pulse at U116-pin3 every 8.3 milliseconds, at least one logic one will be clocked into the flip-flop during the time the 12 millisecond pulse is active. The output of the flip-flop, Pin1, is fed back to its own reset pin through an R-C time delay R118, C121. The net result is that when the flip-flop is clocked with a logic one at the D input, pin5, the output of the flip-flop goes high for 20 milliseconds. 20 milliseconds is the amount of the R-C time delay.

While the output of U116-pin1 is high, the Qbar output is low (pin2). Pin2 is fed back to the clock input to inhibit any further input clock pulses while the Q output is active.

Thus, the output of the U116-pin1 goes high for a single pulse of 20 milliseconds, once every second. Furthermore, the start of the 20 mSec pulse is synchronized with the zero crossing instant of the AC power line voltage. This 20 millisecond pulse is applied to the Io Blank line, commanding the power supply output to be shut off for 20 milliseconds.

The 20 mSec pulse from U116-pin2, also gates the 120 Hz zero crossing pulses through the NAND gate U115 pins 8, 9, 10. Two of the 120 Hz, 200 uSec pulses will be gated through to U115-pin10. This is due to the fact that the zero crossing pulses occur every 8.33 mSec in a 20 millisecond window. Also, the 20 millisecond window is generated immediately following the zero crossing pulse before the window was opened.

The two 200 uSec zero crossing pulses that are gated to U115-pin10 (once every second) are used to pulse the S/H #1 and S/H #2 optoisolators. The flip-flop U116 pins 13, 12 is configured as a divide by two counter. Through the gates U115-pin3 and U115-pin4, a single 200 uSec pulse is applied alternately to S/H #1 and S/H #2.

Thus, S/H #1 is pulsed for 200 uSec, once per second, at the first AC zero crossing following the power supply turn off command (Io Blank). This allows 8.1 milliseconds to turn off the power supply output current before the first Off Potential voltage sample is taken.

S/H #2 is pulsed from 200 uSec, once per second, at the second AC zero crossing following the power supply turn off command.

All control circuits of a plurality of channel controllers would be identical. The schematic for a single channel is shown on FIG. 8.

The connections to the reference half-cell and the steel structure applied to the instrumentation amplifier constructed from the four operational amplifiers in U1. A reference select switch is shown to allow selection of two different input sources.

Noise and high voltage spike filtering is provided by resistors R1, R2 and C1. Additional input voltage clamping for amplifier protection is provided by Zener diodes VR1 to VR4.

Three of the quad op amps in the quad op amp package are configured as a standard instrumentation amplifier. The amplifier will amplify only the voltage difference between the reference and the structure lines, and reject any common mode voltage between these two lines and the amplifier common.

The amplifier also has very high (10's of Megohms) input impedance to minimize the loading on the usually high output impedance of most commercial half-cells.

The overall gain is two. The gain is reduced back to one by the voltage divider R11 and R12. The fourth op amp in U1 is used to buffer the output signal following the resistive divider. The voltage at U1-pin14 is the measured potential of the structure with respect to the half cell. This voltage is optionally available for monitoring at TP1. The measured structure-reference voltage is applied simultaneously to the inputs of three sample and hold IC's. The sample and hold circuits are commanded into the sample mode when the S/H pin 8 goes high. The S/H pins are controlled by the phototransistor in the optoisolator. When the diode of the optoisolator is pulsed by the timing and strobe circuitry, current flows through the phototransistor. This current raises the voltage on the 4.7K resistors connected to the emitters of the phototransistors and commands the sample mode.

The S/H pulses are 200 uSec which is adequate to store an accurate sample. As described previously, the measured barrier voltage is stored in S/H 1 and 2 during the Io Blanking time. S/H 3 is updated at every AC line zero crossing and is optionally used to supply rate information to the control loop. The output of S/H 3 is time averaged through R18 and C11 and then A-C coupled to the control loop error amplifier by C12, C13 and R21. These components are trial values only and must be chosen to suit a given application. In most applications, these components may be left out entirely.

The stored values on S/H's 1 and 2 are fed to the error amplifier summing junction (U7-pin13) through equal resistors R19 and R20. This technique forms an equally weighted sum of the two samples to be fed back to the control system, which is really feeding back the average value of the two samples.

The average value of the measured Off Potential is applied to the error amplifier, U7 pins 12, 13, and 14. The Off Potential is compared to a setpoint (or desired) value which is fed to pin 12 of the error amplifier. The error between the desired Off Potential and the measured average Off Potential is amplified by a D.C. gain of 400 and the amplified error signal appears on U7 pin 14.

C14 is a 10 u F capacitor which provides at roll off in the frequency response of the error amplifier starting at approximately 0.016 Hz. This is done to keep the overall control loop stable due to the relatively long intervals between sample updates (one second). Diode CR8 is used to protect C14, and electrolytic, from reverse bias.

Voltage regulator IC U5 is a stable, adjustable voltage reference. With R23 and R24, it is set for 5.00V output. The absolute accuracy is not as important as the low temperature and time drift of the output voltage. Through buffer op amps U6-pins 5, 6, and 7 and U6-pins 2, 3, and 1, the 5.00 volts is used to generate a stable 10.0 V and −5.0V reference.

The −5.0 and −5.0 volt references are applied to resistor chain R29, R30 and R31. R30 is a precision potentiometer, and the wiper arm may be adjusted to select the desired autopotential to be maintained by the control system. The wiper is buffered by unity gain buffer U6-pins 9, 10 and 8. The autopotential setpoint is available for monitoring at the output of the buffer. The setpoint range varies for +1.0V to −3.0V. The selected setpoint value is inverted in polarity by U6-pins 12, 13 and 14 and applied to the non-inverting input of the error amplifier. The polarity is inverted since the instrumentation amplifier U1 is inverting.

When the autopotential mode is selected, the output of the error amplifier, U7-pin 14, is applied to output buffer U8-pins 2, 3, and 1. The transistor boosted opamp (Q1 boost) is used to drive the current demand signal to the power supply. The transistor buffer allows low impedance drive to any number of parallel power supplies.

When the autopotential switch is selected for autopotential mode, the Io Blank command is connected to the input of the drive buffer. During the Io Blanking time (20 milliseconds), the optoisolator transistor in OC4 is ON and the input to buffer U8 pin3 is grounded through the opto-transistor. This causes the output to go to zero for 20 milliseconds causing the power supply output current to be commanded to zero for 20 milliseconds.

Resistor R42 and capacitor C24 form an R-C time constant to slow the voltage rate of rise to the current demand signal at the end of the 20 millisecond blanking period. This is done to soften the turn on of the power supply to reduce component stress and any ticking audio noise.

VR8 is used to limit the current demand signal to the power supplies to 11V or 110% of maximum rated output.

When the autopotential switch is moved to deselect autopotential mode, the Io Blanking signal is disconnected and the error amplifier is disconnected. Thus, all barrier potential measurements are ignored by the control loop.

In the case of the hybrid implementation, the physical switch to disconnect the error amplifier is eliminated and instead, the error amplifier is forced high (+11V). Diode CRI blocks the error amplifier signal, thus effectively disconnecting it from he output buffer.

The output current from the power supply module is monitored by an external 50 mV meter shunt. The output leads from the shunt are brought to a connector on the controller channel and applied to the amplifier U7-pins 1, 2, and 3. The amplifier is configured as a differential amplifier with a modest amount of common mode rejection. The D.C. gain is set to 200, so that a full scale 50 mV output from the meter shunt appears as a 10V signal at U7-pin1. This is a representation of the output current of the power supply, with 10V representing 100% or full scale output. A potentiometer R67 is used to apply an offset correction current to the amplifier summing junction through resistor R68. This is used to null out any initial offset errors in the amplifier.

The output voltage of the power supply is monitored through resistive divider R56 and R57. The output voltage is divided by three since in the majority of applications, the full scale output voltage is 30V and the controller recognizes 10V as full scale output voltage.

The internal 10.0V reference voltage is applied to potentiometers R45 and R60. These are precision 10 T pots used to manually adjust the desired maximum output voltage and current of the power supply.

The amplified version of the meter shunt reading is compared to the max current setpoint value from the wiper of R60. The comparison is done by amplifier U7-pins 5, 6, and 7. The amplifier has large gain at D.C.

with frequency roll off controlled by R49 and C15 for control loop stability.

When the output current is less than the setpoint value, the output of U7-pin7 is saturated at 11 V. Because of isolation diode CR2, the amplifier is disconnected from the output command buffer U8-pin3. If the power supply current rises to or above the setpoint value, the amplifier U7-pin7 will lower from +11V until CR2 conducts. At this point the current error amplifier will "take over" the control loop and directly control the output voltage of the current demand signal.

The voltage control loop works in an identical way. The desired maximum output voltage is compared to (a scaled version) of the actual power supply output voltage. The comparison is performed by the error amplifier U7-pins 8, 9, and 10. When the output voltage exceeds the setpoint from the wiper of pot R45, the amplifier pin 8 lowers from +11V until CR3 conducts to allow the amplifier to take control of the power supply current demand signal.

Resistor R41 is used to bias the current demand signal to maximum. The current demand signal may then be modified downwards by either of the autopotential error amplifier (if the mode switch is in autopotential mode), the current error amplifier or the voltage error amplifier. The current and voltage error amplifiers remain active in all modes.

An indication of current limiting control or voltage limiting control is provided by a red and green LED. The outputs of the current and voltage error amplifiers are monitored by the dual comparators of IC U9. When the output voltage of current error amplifier, U7-pin7 falls below +10V, it means that the setpoint maximum current has been exceeded and that the control loop is being taken over by the current error amplifier. This is detected by U9-pins 5, 6, and 7. Pin 7 goes low and allows current to flow in the green LED, thus indicating that the controller is limiting output current.

Similarly, the red LED is lit when the voltage error amplifier is controlling output current.

Amplifier U8-pins 5, 6, and 7 allows the sampled Off Potential to be monitored by an external meter for test purposes. The outputs of the two sample and holds U3 and U4 are averaged through resistors R58 and R59, and inverted at pin7. The inversion is done to present the polarity of the barrier potential according to industry standards.

The invention has been described with reference to the preferred embodiment. Obviously, modifications and alterations will occur to others upon the reading and understanding of the specification. It is our intention to include all such modifications and alterations insofar as they come within the scope of the appended claims or the equivalents thereof.

What is claimed is:

1. An assembly for cathodically protecting a structure by impressing a selective electrical potential upon the structure with high frequency switching, said impressing being selectively operable in either a constant current, a constant voltage, or an auto-potential mode, said assembly comprising:
   a source of an alternating voltage power signal;
   a switch mode power circuit means for generating a square wave voltage form the source;
   a power transformer having a primary side winding and a secondary side winding, the primary side winding being driven by the power circuit means, the secondary side winding having a tap to divide the square wave voltage and produce a plurality of selectively phase differentiated square wave voltages;
   a switch means for selectively rectifying the phase differentiated square wave voltages; and,
   a phase control circuit means for selectively delaying the rectifying of the phase differentiated square wave voltages comprising means for delaying operation of the switch means proportionate to a frequency of the differentiated square wave voltages, wherein the switch means is delayed by a controlled phase delay time.

2. The assembly as claimed in claim 1 further including:
   a current measuring circuit means for measuring an actual current form the switch means;
   a current comparator circuit means for comparing the measured actual current with a preselected desired current and generating a signal representative of a difference between the actual current and the desired current; and
   a feedback control circuit means for selectively adjusting the controlled phase delay time as a function of said difference.

3. The assembly as claimed in claim 1 further including an off potential measuring circuit means for measuring a potential of the structure during a testing period comprising a period when current to the structure is momentarily interrupted;
   an off potential comparator circuit means for comparing the measured potential of the structure with a preselected desired potential and generating an off-potential difference signal;
   said feedback control circuit means selectively adjusting the controlled phase delay time of synchronous switches in proportion to the off potential difference signal.

4. The assembly as claimed in claim 1 further including:
   a voltage measuring circuit means for measuring a voltage from the switch means;
   a voltage comparator circuit means for comparing the measured voltage with a preselected desired voltage and generating a signal representative of a difference between the measured voltage and the desired voltage; and,
   a feedback control circuit means for selectively adjusting the controlled phase delay time as a function of said difference.

5. The assembly as claimed in claim 1 further including circuitry whereby said assembly is adapted to be arranged in at least one of a series or parallel configuration with other identical assemblies.

6. The assembly as claimed in claim 1 wherein the high frequency is above commercial line frequency.

7. A method for selectively adjusting the energy impressed on a structure by a cathodic protection system comprising the steps of:
   rectifying a conventionally available energy signal with a high frequency switch-mode power circuit and a synchronous detector switch assembly;
   impressing the rectified signal on the structure;
   measuring a parameter representative of the impressed energy and generating a control signal representative of a difference with the measured energy and a desired energy; and,
   adjusting a timing operation of the switch assembly to selectively adjust the rectified signal whereby the adjusted rectified signal substantially impresses the desired energy on the structure.

8. The method of claim 7 wherein the desired energy comprises a preselected constant voltage impressed on the structure, the measuring comprising measuring the voltage from the switch assembly and adjusting the switch assembly operation to maintain a constant voltage to the structure.

9. The method of claim 8 wherein the desired energy comprises a preselected constant current from the switch means, the measuring comprising measuring the current from the switch assembly and adjusting the switch assembly operation to maintain a constant current to the structure.

10. The method of claim 7 wherein the desired energy comprises a potential of the structure, the measuring comprising measuring a potential of the structure during a testing period when the impression of energy on the structure is momentarily interrupted, and adjusting the switch assembly operation to provide the desired potential.

11. The method of claim 7 further including the step of:
   interconnecting a plurality of said assembly in at least one of a series or parallel configuration.

12. An off-potential method for selectively adjusting the energy impressed on a structure by a cathodic protection system having a high frequency switch mode power circuit and a synchronous detector switch assembly comprising the steps of:
   supplying an energy signal to the structure;
   selectively halting the supply of energy for a preselected period of time including switching the energy signal to obtain opposite phased signals and adding the signals to produce a zero signal;
   measuring the potential difference between the structure and a reference cell during the preselected period, the measuring being substantially I-R drop free;
   comparing the measured potential difference with a preselected desired potential level; and,
   adjusting the supplied energy in a preselected manner.

13. The method of claim 12 wherein a plurality of the measured potential differences are selectively stored and averaged, the comparing comprising comparing an averaged potential difference signal wit the desired potential level.

14. The method of claim 12 wherein the supply of energy has an alternating current power line frequency and further including the steps of:
   synchronizing the halting of the supply of energy to the power line frequency with zero cross-over point; and,
   measuring at least two I-R drop free potential differences on alternate power supply frequency cycles for minimizing power supply interference.

* * * * *